(12) United States Patent
Crawford et al.

(10) Patent No.: US 8,771,974 B2
(45) Date of Patent: *Jul. 8, 2014

(54) METHODS OF DETERMINING THE PRESENCE AND/OR AMOUNT OF A BIOMARKER TO DETERMINE THE PRESENCE, IDENTITY, AND/OR SEVERITY OF A LYSOSOMAL STORAGE OR NEUROLOGICAL DISORDER

(75) Inventors: Brett E. Crawford, Poway, CA (US); Jillian R. Brown, Poway, CA (US); Charles A. Glass, San Diego, CA (US); Jim R. Beitel, San Diego, CA (US); Robin M. Jackman, San Diego, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/550,106

(22) Filed: Jul. 16, 2012

(65) Prior Publication Data

US 2013/0149729 A1   Jun. 13, 2013

Related U.S. Application Data

(63) Continuation of application No. 12/649,110, filed on Dec. 29, 2009, now Pat. No. 8,232,073.

(60) Provisional application No. 61/142,291, filed on Jan. 2, 2009, provisional application No. 61/164,365, filed on Mar. 27, 2009, provisional application No. 61/238,079, filed on Aug. 28, 2009.

(51) Int. Cl.
*C12Q 1/48*   (2006.01)

(52) U.S. Cl.
USPC .................................. 435/15; 435/18; 435/19

(58) Field of Classification Search
USPC ............................................ 435/15, 4, 18, 19
See application file for complete search history.

(56) References Cited

U.S. PATENT DOCUMENTS

| | | | |
|---|---|---|---|
| 5,185,245 A | 2/1993 | Heimer | |
| 6,117,647 A | 9/2000 | Romisch et al. | |
| 6,143,730 A | 11/2000 | Parish et al. | |
| 6,653,285 B1 | 11/2003 | Takashima et al. | |
| 6,852,696 B2 | 2/2005 | Takashima et al. | |
| 6,923,965 B2 | 8/2005 | Takashima et al. | |
| 6,936,424 B1 | 8/2005 | Watkins et al. | |
| 7,651,847 B2 | 1/2010 | Lebrilla et al. | |
| 8,232,073 B2 * | 7/2012 | Crawford et al. | 435/15 |
| 2002/0102737 A1 | 8/2002 | Millington et al. | |
| 2003/0024012 A1 | 1/2003 | Abdennebi-Najar et al. | |
| 2003/0054991 A1 | 3/2003 | Takashima et al. | |
| 2003/0228259 A1 | 12/2003 | Hellerstein | |
| 2004/0138105 A1 | 7/2004 | Takashima et al. | |
| 2005/0159343 A1 | 7/2005 | Takashima et al. | |
| 2005/0238536 A1 | 10/2005 | Striepeke et al. | |
| 2006/0269974 A1 | 11/2006 | Dwek et al. | |
| 2006/0286034 A1 | 12/2006 | Meikle et al. | |
| 2007/0161074 A1 | 7/2007 | Tomatsu et al. | |
| 2008/0071148 A1 * | 3/2008 | Bosques et al. | 600/300 |
| 2008/0153752 A1 | 6/2008 | Takashima et al. | |
| 2010/0184013 A1 * | 7/2010 | Crawford et al. | 435/4 |
| 2012/0009616 A1 | 1/2012 | Crawford et al. | |
| 2012/0289415 A1 * | 11/2012 | Bosques et al. | 506/6 |
| 2013/0149729 A1 * | 6/2013 | Crawford et al. | 435/15 |

FOREIGN PATENT DOCUMENTS

| | | |
|---|---|---|
| GB | 2468386 A | 9/2010 |
| WO | WO 01-31045 A1 | 5/2001 |
| WO | WO 01-36977 A2 | 5/2001 |
| WO | WO 01-94941 A2 | 12/2001 |
| WO | WO 01-94941 A3 | 8/2003 |
| WO | WO 03/092601 A2 | 11/2003 |
| WO | WO 03/106997 A1 | 12/2003 |
| WO | WO 2004-019040 A1 | 3/2004 |
| WO | WO 03/092601 A3 | 9/2004 |
| WO | WO 2007-010089 A2 | 1/2007 |
| WO | WO 2007-010089 A3 | 5/2007 |
| WO | WO 2007/138263 A1 | 12/2007 |
| WO | WO 2010/078511 A2 | 7/2010 |
| WO | WO 2010/078514 A2 | 7/2010 |
| WO | WO 2010/078511 A3 | 10/2010 |

OTHER PUBLICATIONS

An et al., Glucose tetrasaccharide as a biomarker for monitoring the therapeutic response to enzyme replacement therapy for Pompe disease, (2005), Mol. Gen. Metabol, 85:247-254.

An et al., Profiling of glycans in serum for the discovery of potential biomarkers for ovarian cancer, (2006), J. Proteome Res., 5(7):1626-1635.

Byers, S. et al., Glycosaminoglycan accumulation and excretion in the mucopolysaccharidoses: Characterization and basis of a diagnostic test for MPS, (1998), Molecular Genetics and Metabolism, 65(4):282-290.

Calabro, A. et al., Microanalysis of enzyme digests of hyaluronan and chondroitin/dermatan sulfate by fluorophore-assisted carbohydrate electrophoresis (FACE), (2000), Glycobiology, 10(3):273-281.

Calabro, A. et al., Adaptation of FACE methodology for microanalysis of total hyaluronan and chondroitin sulfate composition from cartilage, (2000), Glycobiology, 10(3):283-293.

Daud et al., Synthetic heparin pentasaccharide depolymerization by heparinase 1: Molecular and biological implications, (2001), Clin. Appl. Thromb. Hemost., 7:58-64.

Deakin et al., A simplified and sensitive fluorescent method for disaccharide analysis of both heparin sulfate and chondroitin-dermatan sulfates from biological samples, (2008), Glycobiology, 18:483-491.

Deegan et al., Clinical evaluation of chemokine and enzymatic biomarkers of Gaucher disease, (2005), Blood Cells Mol. Dis., 35(2):259-267.

Delaney et al., A high-performance liquid chromatography approach for isolation and sequencing of chondroitin sulfate oligosaccharides, (1980), Anal. Biochem., 108(1):25-34.

(Continued)

*Primary Examiner* — Ralph Gitomer
(74) *Attorney, Agent, or Firm* — Jones Day

(57) ABSTRACT

Provided herein are methods of diagnosing or monitoring the treatment of abnormal glycan accumulation or a disorder associated with abnormal glycan accumulation.

21 Claims, 4 Drawing Sheets

(56) References Cited

OTHER PUBLICATIONS

Ferro et al., Evidence of conformational equilibrium of the sulfated L-iduronate residue in heparin and in synthetic heparin mono- and oligosaccharides: NMR and force-field studies, (1986), J. Am. Chem. Soc., 108:6778-6784.

Freeman et al., Human α-L-iduronidase, (1992), Biochem. J., 282:899-908.

Fuller et al., Glycosaminoglycan degradation fragments in mucopolysaccharidosis I, (2004), Glycobiology, 14(5):443-450.

Hansen et al., HPLC glycosaminoglycan analysis in patients with Graves' disease, (1997), Clin. Sci., 92:511-517.

Hitchcock, A. et al., Comparative glycomics of connective tissue glycosaminoglycans, (2008), Proteomics, 8(7):1384-1397.

Honda et al., High-performance capillary electrophoresis of unsaturated oligosaccharides derived from glycosaminoglycans by digestion with chondroitinase ABC as 1-phenyl-3 methyl-5-pyrazolone derivatives, (1992), Journal of Chromatography, 608(1):289-295.

Hopwood and Elliott, Urinary excretion of sulphated N-acetylhexosamines in patients with various mucopolysaccharidoses, (1985), Biochem. J., 229:579-586.

Imanari et al., High performance liquid chromatographic analysis of glycosaminoglycan-derived oligosaccharides, (1996), Journal of Chromatography A, 720:275-293.

Jacquinet et al., Synthesis of heparin fragments. A chemical synthesis of the trisaccharide O-(2-deoxy-2-sulfamido-3,6-di-O-sulfo-α-D-glucopyranosyl)-(1-4)-2-deoxy-2-sulfamido-6-O-sulfo-D-glucopyranose heptasodium salt, (1984), Carbo. Res., 130:221-241.

Kimura, A. et al., Chemical structure of urinary dermatan sulfate excreted by a patient with the Hunter syndrome, (1980), Tohoku Journal of Experimental Medicine, 131(3):241-247.

Kimura, A. et al., Fractionation and characterization of urinary heparan sulfate excreted by patients with Sanfilippo syndrome, (1984), Tohoku Journal of Experimental Medicine, 144(3):227-236.

Kirmiz et al., A serum glycomics approach to breast cancer biomarkers, (2007), Mol. Cell. Proteomics, 6(1):43-55.

Kodama C. et al., High-performance liquid chromatography of pyridylamino derivatives of unsaturated disaccharides produced from chondroitin sulfate isomers by chondroitinases, (1984), Journal of Biochemistry, 96(4):1283-1287.

Kodama C. et al., Liquid-chromatographic determination of urinary glycosaminoglycans for differential diagnosis of genetic mucopolysaccharidoses, (1986), Clin. Chem., 31(1 Pt 1):30-34.

Lawrence, R. et al., Evolutionary differences in glycosaminoglycan fine structure detected by quantitative glycan reductive isotope labeling, (2008), J. Biol. Chem., 283(48):33674-33684.

MacCari et al., Anomolous structure of urinary glycosaminoglycans in patients with pseudoxanthoma elasticum, (2003), Clin. Chem., 49:380-388.

Mao et al., Capillary electrophoresis for the analysis of glycosaminoglycans and glycosaminoglycan-derived oligosaccharides, (2002), Biomedical Chromatography, 16:77-94.

Mason et al., Characterization of sulfated oligosaccharides in mucopolysaccharidosis type IIIA by electrospray ionization mass spectrometry, (2006), Anal. Chem., 78(13):4534-4542.

Minamisawa et al., Microscale preparation of even- and odd-numbered N-acetylheparosan oligosaccharides, (2006), Carbo. Res., 341:230-237.

Minamisawa et al., Systematic identification of N-acetylheparosan oligosaccharides by tandem mass spectrometric fragmentation, (2006), Rapid Commun. Mass Spectrom., 20:267-274.

Nader, H. et al., Chemistry of heparitin sulfate and heparin from normal tissues and from patients with Hunter syndrome, (1979), Biochim. et. Biophys. Acta, 582(1):33-43.

Nomenclature Committee Consortium for Functional Glycomics "Symbol and Text Nomenclature for Representation of Glycan Structure" (May 2012) accessed on internet on Sep. 12, 2012 at http://www.functionalglycomics.org/static/consortium/Nomenclature.shtml.

Plaas, A. et al., Glycosaminoglycan sulfation in human osteoarthritis: Disease-related alterations at the non-reducing termini of chondroitin and dermatan sulfate, (1998), J. Biol. Chem., 273(20):12642-12649.

Pol-Fachin and Verli, Depiction of the forces participating in the 2-O-sulfo-α-L-iduronic acid conformational preference in heparin sequences in aqueous solutions, (2008), Carbo. Res., 343:1435-1445.

Rhomberg et al., Mass spectrometric evidence for the enzymatic mechanism of the depolymeriza on of heparin-like glycosaminoglycans by heparinase II, (1998), Proc. Natl. Acad. USA, 95:12232-12237.

Thanawiroon, C. et al., Liquid chromatography/mass spectrometry sequencing approach for highly sulfated heparin-derived oligosaccharides, (2004), J. Biol. Chem., 279(4):2608-2615.

Thompson et al., Oligosaccharide substrates for heparin sulfamidase, (1986), Anal. Chem., 152:412-422.

Toma, L. et al., Differences in the non-reducing ends of heparan sulfates excreted by patients with mucopolysaccharidoses revealed by bacterial heparitinases: A new tool for structural studies and differential diagnosis of Sanfilippo's and Hunter's syndromes, (1996), Laboratory Investigation, 75(6): 771-781.

Volpi et al., Mass spectrometry for the characterization of unsulfated chondroitin oligosaccharides from 2-mers to 16-mers. Comparison with hyaluronic acid oligomers, (2008), Rapid Commun. Mass Spectrom., 22:3526-3530.

Yamada et al., Structural studies on the tri- and tetrasaccharides isolated from porcine intestinal heparin and characterization of heparinase/heparitinases using them as substrates, (1994), Glycobiology, 4(1):69-78.

Yan et al., Prediction and simulation on interaction between HIV-1 envelope protein gp120 and heparin, Chem. J. Chinese U., (2004), 25(3):522-525 (in Chinese with English abstract).

Yosizawa, Z. et al., A simple method for the quantitation of glycuronic acid-containing glycosaminoglycans with mucopolysaccharidases, (1983), Analytical Biochemistry, 128(1):250-256.

International Search Report for PCT/US2009/069941 mailed Aug. 27, 2010.

International Search Report for PCT/US2009/069944 mailed Aug. 31, 2010.

International Search Report and Written Opinion for PCT/US2009/069946 dated Sep. 9, 2012.

Matzner et al., Enzyme replacement improves nervous system pathology and function in a mouse model for metachromatic leukodystrophy. Hum Mol Genet, May 1, 2005, vol. 14, No. 9.

Mahuran, Biochemical consequences of mutations causing the GM2 gangliosidoses. Biochim Biophys Acta, Oct. 8, 1999, vol. 1455, No. 2-3, pp. 105-38.

International Search Report for PCT/US13/61914 mailed Dec. 17, 2013.

\* cited by examiner

US 8,771,974 B2

METHODS OF DETERMINING THE PRESENCE AND/OR AMOUNT OF A BIOMARKER TO DETERMINE THE PRESENCE, IDENTITY, AND/OR SEVERITY OF A LYSOSOMAL STORAGE OR NEUROLOGICAL DISORDER

CROSS-REFERENCE

This application is a continuation application of Ser. No. 12/649,110 filed Dec. 29, 2009, now U.S. Pat. No. 8,232,073 which application claims the benefit of U.S. Provisional Application No. 61/142,291, filed 2 Jan. 2009, U.S. Provisional Application No. 61/164,365, filed 27 Mar. 2009, and U.S. Provisional Application No. 61/238,079, filed 28 Aug. 2009, which applications are incorporated herein by reference.

BACKGROUND OF THE INVENTION

Many human diseases are caused by or correlated with changes in glycosylation. In order to use these changes as biomarkers of disease, analytical methods are used to quantify the changes. The published methods use antibodies, chromatography and/or mass spectrometry techniques to resolve and quantify the intact or partially intact glycans. These methods are challenging due to the complexity and number of possible glycan structures present in biological samples. In a single disease state there can be thousands of different novel glycan structures that are present; however, each on their own is a weak marker of disease.

SUMMARY OF THE INVENTION

Described herein are populations of glycans that are transformed into populations of biomarkers using glycan degradation enzymes. Further described herein are the use of analytical instruments to characterize the population of biomakers (i.e., non-reducing end glycan residual compounds, such as monosaccharides) in order to provide relevant information about the population of biomarkers, the population of biomarkers and the biological sample that provided the population of biomarkers.

Provided in certain embodiments herein are methods of detecting glycan accumulation and/or abnormal glycan biosynthesis and/or degradation in a biological sample, the method comprising:
 a. transforming a glycan of a biological sample with a glycan degradation enzyme to liberate a glycan residual compound from the non-reducing end of the glycan;
 b. measuring the amount of the glycan residual compound liberated by the functioning glycan degradation enzyme with an analytical device.

In some embodiments, a method described herein comprises a method of diagnosing an individual as having a disease or condition associated with abnormal glycan biosynthesis, degradation, or accumulation, the method comprising:
 a. generating a biomarker comprising of one or more non-reducing end glycan residual compound, wherein the biomarker is generated by treating a population of glycans, in or isolated from a biological sample from the individual, with at least one digesting glycan enzymes, wherein prior to enzyme treatment, the biomarker is not present in abundance in samples from individuals with the disease or condition relative to individuals without the disease or condition, and
 b. using an analytical instrument to detect the presence of and/or measure the amount of the biomarker produced and displaying or recording the presence of or a measure of a population of the biomarker;

In some embodiments, the presence of and/or measure the amount of the biomarker is utilized to determine the presence, identity, and/or severity of the disease or condition.

Provided in certain embodiments herein is a method of diagnosing an individual as having a disease or condition associated with abnormal glycan biosynthesis, degradation, or accumulation, the method comprising:
 a. transforming a glycan of a biological sample with a glycan degradation enzyme to liberate a glycan residual compound from the non-reducing end of the glycan;
 b. measuring the amount of the glycan residual compound liberated by the functioning glycan degradation enzyme with an analytical device; and
 c. determining whether the amount of liberated glycan residue is abnormal.

In some embodiments, provided herein is a method of monitoring the treatment of a disorder associated with the abnormal degradation, biosynthesis and/or accumulation of glycans, the method comprising:
 a. following administration of an agent for treating a disorder associated with the abnormal degradation, biosynthesis and/or accumulation of glycans to an individual in need thereof, using an analytical instrument to measure the amount of a population of a biomarker comprising a non-reducing end glycan residual compounds present in a transformed biological sample, the biomarker being generated by treating a population of glycans, in or isolated from a biological sample from the individual, with at least one digesting glycan enzyme(s), wherein prior to enzyme treatment, the biomarker is not present in abundance in samples from individuals with the disease or condition relative to individuals without the disease or condition, and
 b. determining whether or not the amount of the amount of biomarker has decreased or increased at a slower rate compared to the amount or rate of increase prior to administration of the agent for treating a disorder associated with the abnormal degradation, biosynthesis and/or accumulation of glycans.

In some embodiments, the abnormal glycan accumulation or disorder associated therewith is caused by an abnormally functioning glycan degradation enzyme and wherein the abnormally functioning glycan degradation enzyme and glycan degradation enzyme are of the same type (e.g., the glycan degradation utilized in the transformation process is a functioning glycan degradation enzyme whereas the abnormally functioning enzyme is not, such as due to deletions, insertions, substitutions, or other modifications to the enzyme sequence). In certain embodiments, the abnormally functioning glycan degradation enzyme functions abnormally as a result of being present in an abnormally low amount, functioning improperly, or a combination thereof. In some embodiments, the abnormal glycan accumulation comprises the accumulation of abnormal amounts of glycans. In certain embodiments, the abnormal glycan accumulation comprises the accumulation of abnormal amounts of normal glycans. In some embodiments, the abnormal glycan accumulation comprises the accumulation of abnormal amounts of abnormal glycans.

In certain embodiments, the biomarker is not present in the original biological sample. In some embodiments, the biomarker is not present in the biological sample after isolating a population of glycans therefrom (e.g., prior to transformation of the glycan according to a process described herein).

In certain embodiments, the normally functioning glycan degradation enzyme is a glycosidase, sulfatase, phosphorylase, deacetylase or a combination thereof. In some embodiments, the normally functioning glycan degradation enzyme is a glycosidase selected from an exo-glycosidase and an endo-glycosidase. In certain embodiments, the glycosidase is an exo-glycosidase selected from the group consisting of a galactosidase, and a glucuronidase. In some embodiments, the generated biomarker is a glycan residual compound. In some embodiments, the glycan residual compound is a monosaccharide. In certain embodiments, the glycan residual compound is sulfate, phosphate, acetate, or a combination thereof. In certain embodiments, the glycan residual compound has a molecular weight of less than 2000 g/mol, less than 1500 g/mol, less than 1000 g/mol, less than 500 g/mol, less than 400 g/mol, less than 300 g/mol, less than 260 g/mol, less than 200 g/mol, less than 100 g/mol, or the like (e.g., prior to tagging with any detectable label that may be included in a process described herein).

In some embodiments, any process described herein further comprises purifying a biological sample prior to transforming a glycan thereof. In some embodiments, the process of purifying a biological sample comprises removing monosaccharides therefrom, removing sulfates therefrom, removing phosphates therefrom, removing acetate therefrom, or a combination thereof.

In certain embodiments, transforming a glycan of a biological sample with a normally functioning glycan degradation enzyme comprises transforming a glycan of a biological sample with a plurality of normally functioning glycan degradation enzymes. In some embodiments, the glycan is treated with a plurality of normally functioning glycan degradation enzymes concurrently, sequentially, or a combination thereof.

In specific embodiments, a disorder associated with an abnormal glycan accumulation is any disorder described in Tables 1-4 (e.g., MPS I) and the normally functioning glycan degradation enzyme is any enzyme described in Tables 1-4 (e.g., L-iduronidase).

In some embodiments, determining whether the amount of liberated glycan residue is abnormal comprises labeling the glycan residue with a detectable label and measuring the amount of labeled glycan residue with an analytical instrument. In certain embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

Provided in some embodiments herein is a method of monitoring the treatment of a disorder associated with the abnormal degradation, biosynthesis and/or accumulation of glycans, the methods comprising:
    a. following administration of an agent for treating a disorder associated with the abnormal degradation, biosynthesis and/or accumulation of glycans to an individual in need thereof, using an analytical instrument to measure the amount of a population of a non-reducing end glycan residual compounds present in a transformed biological sample that has been prepared by:
        treating a population of glycans, in or isolated from a biological sample taken from the individual, with at least one normally functioning glycan degradation enzyme to liberate non-reducing end glycan residual compound;
    b. determining whether or not the amount of the amount of liberated non-reducing end glycan residue has decreased or increased at a slower rate compared to the amount or rate of increase prior to administration of the agent for treating a disorder associated with the abnormal degradation, biosynthesis and/or accumulation of glycans.

In some embodiments, the disorder associated with the abnormal degradation, biosynthesis and/or accumulation of glycans is a lysosomal storage disease, a cancerous disease, or an infectious disease. In certain embodiments, the normally functioning glycan degradation enzyme is a glycosidase, sulfatase, phosphorylase, deacetylase, or a combination thereof. In some embodiments, the normally functioning glycan degradation enzyme is a glycosidase selected from an exo-glycosidase and an endo-glycosidase. In certain embodiments, the glycan residual compound is a monosaccharide, sulfate, phosphate, acetate, or a combination thereof. In some embodiments, transforming a glycan of a biological sample with a normally functioning glycan degradation enzyme comprises transforming a glycan of a biological sample with a plurality of normally functioning glycan degradation enzymes. In certain embodiments, the glycan is treated with a plurality of normally functioning glycan degradation enzymes concurrently, sequentially, or a combination thereof. In some embodiments, prior to measuring the amount of a population of non-reducing end glycan residual compounds, the non-reducing end glycan residual compounds are labeled with a detectable label. In certain embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
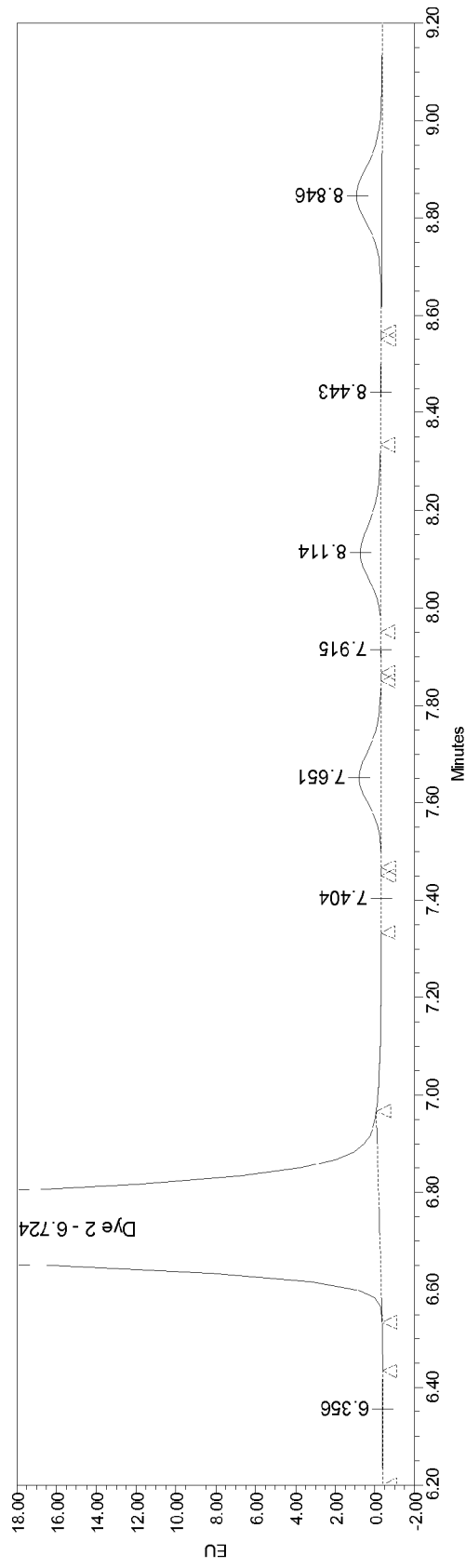
FIG. 1 illustrates compounds present in a normal biological sample not subject to an enzymatic glycan residual liberation process described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Provided herein is a method of detecting abnormal glycan accumulation, e.g., in human disease. In some instances, the process described herein includes a strategy to quantify the changes by measuring the abundance of all glycans with a disease related glycan residual compound on the non-reducing end of glycans from a biological sample (e.g., monosaccharides and/or their modifications such as sulfation, acetylation, phosphorylation, or the like).

Provided in certain embodiments herein are methods of detecting glycan accumulation in a biological sample, the method comprising:
  a. transforming a glycan of a biological sample with a normally functioning glycan degradation enzyme to liberate a glycan residual compound from the non-reducing end of the glycan;
  b. measuring the amount of the glycan residual compound liberated by the functioning glycan degradation enzyme with an analytical device.

In certain embodiments, the method is associated with diagnosing an individual with abnormal glycan accumulation, or a disorder associated therewith.

Therefore, in specific embodiments, provided herein is a method of diagnosing an individual as having an abnormal glycan accumulation or a disorder associated with an abnormal glycan accumulation, the method comprising:
  a. transforming a glycan of a biological sample with a normally functioning glycan degradation enzyme to liberate a glycan residual compound from the non-reducing end of the glycan;
  b. measuring the amount of the glycan residual compound liberated by the functioning glycan degradation enzyme with an analytical device; and
  c. determining whether the amount of liberated glycan residue is abnormal.

In certain instances, methods of detecting abnormal glycan accumulation works based on the observation that altered glycans generated in a disease state are caused by an alteration in the activity of a biosynthetic enzyme (e.g., via increased expression, increased activity, increased substrate, or the like) that leads to the production of thousands of unique structures.

For example, in certain instances, the induction of an alpha 2,3 sialyltransferase leads to the novel expression of thousands of different glycans (potentially from multiple glycan classes) that present a non-reducing terminal alpha 2,3 linked sialic acid. By quantifying a limited set of these novel structures using current methods, only a fraction of the disease related structures are measured. Instead, as provided in certain embodiments herein, if a sample containing glycans (crude or purified for a specific glycan class) is treated with an alpha 2,3 sialidase to liberate the non-reducing end sialic acid, the free sialic acid (non-reducing end glycan residual) can be measured. This signal would represent a larger portion of the thousands of altered glycan structures that are made in the disease state due to the altered expression of the alpha 2,3 sialyltransferase. Furthermore, in certain embodiments, depending on the signal (i.e., measurement) of the sialic acid liberated, a determination is made as to whether or not the accumulation of sialic acid is abnormal and/or whether or not such levels of accumulated sialic acid is associated with a disorder.

Another example of the process includes a method involving a biological sample containing glycans (purified or not) that is treated with an exo-glycosidase (for example a β-galactosidase). In some of such embodiments, enzymatic treatment cleaves non-reducing end monosaccharides within the chosen enzymes specificity (e.g., β-linked galactose residues) and liberates them as free monosaccharide (e.g., galactose). In various embodiments, the free monosaccharide is isolated and quantified by any analytical method (HPLC, MS, GC, etc), and any disease that presents changes in the levels of non-reducing end O-linked galactose residues is detected or diagnosed.

Similar methods are also optionally utilized in methods of monitoring and/or determining the therapeutic of a treatment or treatment regimen, particularly in the treatment of a disorder associated with abnormal glycan accumulation. For example, provided in certain embodiments herein is a method of monitoring the treatment of disorders associated with the abnormal degradation, biosynthesis and/or accumulation of glycans, the methods comprising:
  a. following administration of an agent for treating a disorder associated with the abnormal degradation, biosynthesis and/or accumulation of glycans to an individual in need thereof, using an analytical instrument to measure the amount of a population of a non-reducing end glycan residue present in a transformed biological sample that has been prepared by:
      treating a population of glycans, in or isolated from a biological sample taken from the individual, with at least one normally functioning glycan degradation enzyme to liberate non-reducing end glycan residue;
  b. determining whether or not the amount of the amount of liberated non-reducing end glycan residue has decreased or increased at a slower rate compared to the amount or rate of increase prior to administration of the agent for treating a disorder associated with the abnormal degradation, biosynthesis and/or accumulation of glycans.

In some embodiments, any process described herein comprises:
  a. comparing an amount of a population of one or more glycan residual compound present in a transformed biological sample to an amount of a population of one or more glycan residual compound present in a control biological sample that has been treated in a manner substantially similar to the transformed biological sample.

In certain embodiments, a control biological sample utilized in any process described herein was provided from an individual that does not suffer from a disorder being diagnosed. In other embodiments, a control biological sample is taken from an individual suffering from a disorder being diagnosed. In certain embodiments, the result obtained from the control biological sample is stored in a database. In such cases a test sample is optionally compared to a plurality of control data in a database. Moreover in certain embodiments, any diagnostic process described herein is optionally utilized alone or in combination with other diagnostic techniques. Other diagnostic techniques include, by way of non-limiting example, symptom analysis, biopsies, detection of accumulation of other compounds in biological samples, or the like. In some embodiments, control biological samples are optionally taken from the same individual at substantially the same time, simply from a different location (e.g., one inflamed/arthritic synovial joint fluid vs the contralateral non-arthritic synovial joint). In other embodiments, control biological samples are optionally taken from the same individual at different points in time (e.g., before therapy and after therapy if the method being utilized is a method of monitoring a treatment therapy).

Glycan Accumulation:

In various instances, glycan accumulation occurs in a biological sample as a result natural glycan biosynthetic and/or degradation processes. In some instances, abnormal glycan accumulation occurs in a biological sample as a result of a disorder or disease within an individual from which the biological sample is obtained.

In certain embodiments, abnormal glycan accumulation that is observable by methods described herein is associated with the accumulation of glycans in a manner that does not normally occur in individuals who are not in a disease state.

In some embodiments, such accumulation includes the accumulation of abnormal glycans. In certain instances, these abnormal glycans include glycans that are not normally produced in an individual, or a particular biological sample thereof, in the absence of a particular disease state. Therefore, in some embodiments, abnormal glycan accumulation includes the accumulation of glycans, the glycans being abnormal themselves, especially in any significant quantity. In other words, such glycans are abnormal glycans in individuals or particular biological samples thereof when such individuals are in a non-diseased, normal, or wild type state.

In some embodiments, such accumulation includes the abnormal accumulation of glycans. In some instances, these glycans are glycans that normally occur in individuals in a non-diseased state, but at lower or higher levels or are abnormal only due to the location wherein they are produced. Therefore, in some embodiments, abnormal glycan accumulation includes the accumulation of abnormal amounts of glycans or the location thereof, the glycans being normally occurring or abnormal glycans. In other words, the amount of glycan accumulation is abnormal in individuals, or particular biological samples thereof, when such individuals are in a non-diseased, normal, or wild type state.

Biological Sample:

Biological samples suitable for analysis according to the methods and processes described herein include, by way of non-limiting example, blood, serum, urine, hair, saliva, skin, tissue, plasma, cerebrospinal fluid (CSF), amniotic fluid, nipple aspirate, sputum, tears, lung aspirate, semen, feces, synovial fluid, nails, or the like. In specific embodiments, the biological samples suitable for analysis according to the methods and processes described herein include, by way of non-limiting example, urine, serum, plasma, or CSF. In certain embodiments, processes for detecting glycan in a sample comprise providing, from the individual, a test biological sample that comprises glycan. In some embodiments, providing a test biological sample from an individual includes obtaining the sample from the individual or obtaining the sample from another source (e.g., from a technician or institution that obtained the sample from the individual). In some embodiments, the biological sample is obtained from any suitable source, e.g., any tissue or cell (e.g., urine, serum, plasma, or CSF) of an individual. In certain embodiments, the tissue and/or cell from which the glycans are recovered is obtained from liver tissue or cells, brain tissue or cells, kidney tissue or cells, or the like.

In certain embodiments, a biological sample according to any process described herein is taken from any individual. In some embodiments, the individual is an individual suspected of suffering from a disorder associated with abnormal glycan accumulation, biosynthesis, and/or degradation. In certain embodiments, the individual is a newborn or fetus.

In some embodiments, provided herein is a composition comprising isolated glycans, whererein the glycans were isolated from a biological sample, and one or more glycan degradation enzyme. In certain embodiments, the composition further comprises one or more biomarker generated according to any method described herein (e.g., wherein the biomarker is a non-reducing end glycan residual compound). In certain embodiments, provided herein is a biomarker described herein (e.g., a labeled or non-labeled non-reducing end glycan residual compound) and an analytical instrument or chromatographic resin.

Degradation Enzymes:

In certain embodiments, any suitable enzyme is optionally utilized in order to remove a glycan residual compound from the non-reducing end of a glycan. In certain disorders, e.g., as described herein, various types of abnormal glycan accumulation occurs. In certain instances, this type of glycan accumulation is detected and/or measured utilizing any suitable enzyme, e.g., as described herein. For example, Tables 1-4 illustrate various enzymes that are utilized in various embodiments of the processes described herein. Any enzyme with the desired specificity is optionally utilized in any process herein (i.e., to liberate the non-reducing end structures). Enzymes suitable for use in the processes described herein include, by way of non-limiting example, eukaryotic, prokaryotic, native, or recombinant enzymes.

In certain embodiments, a disorder associated with abnormal glycan accumulation includes a disorder associated therewith is caused by an abnormally functioning glycan degradation enzyme. In various embodiments, the abnormally functioning glycan degradation enzyme functions abnormally as a result of being present in an abnormally low amount, functioning improperly, or a combination thereof. For example, an abnormally functioning glycan degradation enzyme functions abnormally as a result of being present in an amount of less than 50%, less than 40%, less than 30%, less than 20%, less than 10%, or less than 5% than is present in an individual with normal amounts of the glycan degradation enzyme (e.g., an individual in a non-diseased, normal, or wild type state). In further or alternative embodiments, abnormally functioning glycan degradation enzymes are present in a normal amount, but do not function properly in degrading glycans. For example, such enzymes may be have amino acid substitutions in the sequences thereof that reduce or eliminate the glycan degradative properties of the enzyme.

In some embodiments, wherein abnormal glycan accumulation results, at least partially from, an abnormally functioning glycan degradation enzyme, a normally functioning glycan degradation is optionally utilized, particularly wherein the abnormally functioning glycan degradation enzyme and the normally functioning glycan degradation enzyme are of the same type.

Normally functioning glycan degradation enzymes that are used in various embodiments described herein include, by way of non-limiting example, glycosidases, sulfatases, phosphorylases, deacetylases, sialidases, or combinations thereof. In more specific embodiments, a normally functioning glycan degradation enzyme is a glycosidase, e.g., an exo-glycosidase or an endo-glycosidase. In more specific embodiments, the glycosidase is an exo-glycosidase, e.g., galactosidase, and a glucuronidase. In some embodiments, such enzymes serve to remove various glycan residual compounds, such as, monosaccharides, sulfate, phosphate, acetate, sialic acid, or combinations thereof, which are detected and/or measured in methods described herein.

In certain embodiments, one or normally functioning glycan degradation enzyme is optionally utilized to liberate a targeted glycan residual compound. Multiple enzyme treatments of glycans within a biological sample are useful in various embodiments, e.g., wherein a particular enzyme is unable to liberate a targeted residual glycan compound without first modifying the non-reducing end of the glycan. For example, a first enzyme is optionally utilized to remove a sulfate so that a second enzyme can be utilized to remove a monosaccharide. In various embodiments, the glycans are treated with a plurality of normally functioning glycan degradation enzymes concurrently, sequentially, or a combination thereof.

Various enzymes that are used in various embodiments of the methods described herein include, by way of non-limiting example, a glycosidase. Non-limiting examples of glycosidase that are optionally utilized in the methods described herein include, by way of non-limiting example, enzymes categorized as 3.2.1.X by BRENDA (the comprehensive Enzyme Information System) including 3.2.1.1 alpha-amylase, 3.2.1.B1 extracellular agarase, 3.2.1.2 beta-amylase, 3.2.1.3 glucan 1,4-alpha-glucosidase, 3.2.1.4 cellulase, 3.2.1.5 licheninase, 3.2.1.6 endo-1,3(4)-beta-glucanase, 3.2.1.7 inulinase, 3.2.1.8 endo-1,4-beta-xylanase, 3.2.1.9 amylopectin-1,6-glucosidase, 3.2.1.10 oligo-1,6-glucosidase, 3.2.1.11 dextranase, 3.2.1.12 cycloheptaglucanase, 3.2.1.13 cyclohexaglucanase, 3.2.1.14 chitinase, 3.2.1.15 polygalacturonase, 3.2.1.16 alginase, 3.2.1.17 lysozyme, 3.2.1.18 exo-alpha-sialidase, 3.2.1.19 heparinase, 3.2.1.20 alpha-glucosidase, 3.2.1.21 beta-glucosidase, 3.2.1.22 alpha-galactosidase, 3.2.1.23 beta-galactosidase, 3.2.1.24 alpha-mannosidase, 3.2.1.25 beta-mannosidase, 3.2.1.26 beta-fructofuranosidase, 3.2.1.27 alpha-1,3-glucosidase, 3.2.1.28 alpha,alpha-trehalase, 3.2.1.29 chitobiase, 3.2.1.30 beta-D-acetylglucosaminidase, 3.2.1.31 beta-glucuronidase, 3.2.1.32 xylan endo-1,3-beta-xylosidase, 3.2.1.33 amylo-alpha-1,6-glucosidase, 3.2.1.34 chondroitinase, 3.2.1.35 hyaluronoglucosaminidase, 3.2.1.36 hyaluronoglucuronidase, 3.2.1.37 xylan 1,4-beta-xylosidase, 3.2.1.38 beta-D-fucosidase, 3.2.1.39 glucan endo-1,3-beta-D-glucosidase, 3.2.1.40 alpha-L-rhamnosidase, 3.2.1.41 pullulanase, 3.2.1.42 GDP-glucosidase, 3.2.1.43 beta-L-rhamnosidase, 3.2.1.44 fucoidanase, 3.2.1.45 glucosylceramidase, 3.2.1.46 galactosylceramidase, 3.2.1.47 galactosylgalactosylglucosylceramidase, 3.2.1.48 sucrose alpha-glucosidase, 3.2.1.49 alpha-N-acetylgalactosaminidase, 3.2.1.50 alpha-N-acetylglucosaminidase, 3.2.1.51 alpha-L-fucosidase, 3.2.1.52 beta-N-acetylhexosaminidase, 3.2.1.53 beta-N-acetylgalactosaminidase, 3.2.1.54 cyclomaltodextrinase, 3.2.1.55 alpha-N-arabinofuranosidase, 3.2.1.56 glucuronosyl-disulfoglucosamine glucuronidase, 3.2.1.57 isopullulanase, 3.2.1.58 glucan 1,3-beta-glucosidase, 3.2.1.59 glucan endo-1,3-alpha-glucosidase, 3.2.1.60 glucan 1,4-alpha-maltotetraohydrolase, 3.2.1.61 mycodextranase, 3.2.1.62 glycosylceramidase, 3.2.1.63 1,2-alpha-L-fucosidase, 3.2.1.64 2,6-beta-fructan 6-levanbiohydrolase, 3.2.1.65 levanase, 3.2.1.66 quercitrinase, 3.2.1.67 galacturan 1,4-alpha-galacturonidase, 3.2.1.68 isoamylase, 3.2.1.69 amylopectin 6-glucanohydrolase, 3.2.1.70 glucan 1,6-alpha-glucosidase, 3.2.1.71 glucan endo-1,2-beta-glucosidase, 3.2.1.72 xylan 1,3-beta-xylosidase, 3.2.1.73 licheninase, 3.2.1.74 glucan 1,4-beta-glucosidase, 3.2.1.75 glucan endo-1,6-beta-glucosidase, 3.2.1.76 L-iduronidase, 3.2.1.77 mannan 1,2-(1,3)-alpha-mannosidase, 3.2.1.78 mannan endo-1,4-beta-mannosidase, 3.2.1.79 alpha-L-arabinofuranoside hydrolase, 3.2.1.80 fructan beta-fructosidase, 3.2.1.81 beta-agarase, 3.2.1.82 exo-poly-alpha-galacturonosidase, 3.2.1.83 kappa-carrageenase, 3.2.1.84 glucan 1,3-alpha-glucosidase, 3.2.1.85 6-phospho-beta-galactosidase, 3.2.1.86 6-phospho-beta-glucosidase, 3.2.1.87 capsular-polysaccharide endo-1,3-alpha-galactosidase, 3.2.1.88 beta-L-arabinosidase, 3.2.1.89 arabinogalactan endo-1,4-beta-galactosidase, 3.2.1.90 arabinogalactan endo-1,3-beta-galactosidase, 3.2.1.91 cellulose 1,4-beta-cellobiosidase, 3.2.1.92 peptidoglycan beta-N-acetylmuramidase, 3.2.1.93 alpha,alpha-phosphotrehalase, 3.2.1.94 glucan 1,6-alpha-isomaltosidase, 3.2.1.95 dextran 1,6-alpha-isomaltotriosidase, 3.2.1.96 mannosyl-glycoprotein endo-beta-N-acetylglucosaminidase, 3.2.1.97 glycopeptide alpha-N-acetylgalactosaminidase, 3.2.1.98 glucan 1,4-alpha-maltohexaosidase, 3.2.1.99 arabinan endo-1,5-alpha-L-arabinosidase, 3.2.1.100 mannan 1,4-mannobiosidase, 3.2.1.101 mannan endo-1,6-alpha-mannosidase, 3.2.1.102 blood-group-substance endo-1,4-beta-galactosidase, 3.2.1.103 keratan-sulfate endo-1,4-beta-galactosidase, 3.2.1.104 steryl-beta-glucosidase, 3.2.1.105 3alpha(S)-strictosidine beta-glucosidase, 3.2.1.106 mannosyl-oligosaccharide glucosidase, 3.2.1.107 protein-glucosylgalactosylhydroxylysine glucosidase, 3.2.1.108 lactase, 3.2.1.109 endogalactosaminidase, 3.2.1.110 mucinaminylserine mucinaminidase, 3.2.1.111 1,3-alpha-L-fucosidase, 3.2.1.112 2-deoxyglucosidase, 3.2.1.113 mannosyl-oligosaccharide 1,2-alpha-mannosidase, 3.2.1.114 mannosyl-oligosaccharide 1,3-1,6-alpha-mannosidase, 3.2.1.115 branched-dextran exo-1,2-alpha-glucosidase, 3.2.1.116 glucan 1,4-alpha-maltotriohydrolase, 3.2.1.117 amygdalin beta-glucosidase, 3.2.1.118 prunasin beta-glucosidase, 3.2.1.119 vicianin beta-glucosidase, 3.2.1.120 oligoxyloglucan beta-glycosidase, 3.2.1.121 polymannuronate hydrolase, 3.2.1.122 maltose-6'-phosphate glucosidase, 3.2.1.123 endoglycosylceramidase, 3.2.1.124 3-deoxy-2-octulosonidase, 3.2.1.125 raucaffricine beta-glucosidase, 3.2.1.126 coniferin beta-glucosidase, 3.2.1.127 1,6-alpha-L-fucosidase, 3.2.1.128 glycyrrhizinate beta-glucuronidase, 3.2.1.129 endo-alpha-sialidase, 3.2.1.130 glycoprotein endo-alpha-1,2-mannosidase, 3.2.1.131 xylan alpha-1,2-glucuronosidase, 3.2.1.132 chitosanase, 3.2.1.133 glucan 1,4-alpha-maltohydrolase, 3.2.1.134 difructose-anhydride synthase, 3.2.1.135 neopullulanase, 3.2.1.136 glucuronoarabinoxylan endo-1,4-beta-xylanase, 3.2.1.137 mannan exo-1,2-1,6-alpha-mannosidase, 3.2.1.138 anhydrosialidase, 3.2.1.139 alpha-glucuronidase, 3.2.1.140 lacto-N-biosidase, 3.2.1.141 4-alpha-D-{(1→4)-alpha-D-glucano}trehalose trehalohydrolase, 3.2.1.142 limit dextrinase, 3.2.1.143 poly(ADP-ribose) glycohydrolase, 3.2.1.144 3-deoxyoctulosonase, 3.2.1.145 galactan 1,3-beta-galactosidase, 3.2.1.146 beta-galactofuranosidase, 3.2.1.147 thioglucosidase, 3.2.1.148 ribosylhomocysteinase, 3.2.1.149 beta-primeverosidase, 3.2.1.150 oligoxyloglucan reducing-end-specific cellobiohydrolase, 3.2.1.151 xyloglucan-specific endo-beta-1,4-glucanase, 3.2.1.152 mannosylglycoprotein endo-beta-mannosidase, 3.2.1.153 fructan beta-(2,1)-fructosidase, 3.2.1.154 fructan beta-(2,6)-fructosidase, 3.2.1.155 xyloglucan-specific exo-beta-1,4-glucanase, 3.2.1.156 oligosaccharide reducing-end xylanase, 3.2.1.157 iota-carrageenase 3.2.1.158 alpha-agarase, 3.2.1.159 alpha-neoagaro-oligosaccharide hydrolase, 3.2.1.160 xyloglucan-specific exo-beta-1,4-glucanase, 3.2.1.161 beta-apiosyl-beta-glucosidase, 3.2.1.162 lambda-carrageenase, 3.2.1.163 1,6-alpha-D-mannosidase, 3.2.1.164 galactan endo-1,6-beta-galactosidase, 3.2.1.165 exo-1,4-beta-D-glucosaminidase, or a combination thereof.

Other enzymes that are used in various embodiments of the methods described herein include, by way of non-limiting example, a sulfatase including, e.g., enzymes categorized as 3.1.6.X by BRENDA (the comprehensive Enzyme Information System) including 3.1.6.1 arylsulfatase, 3.1.6.2 steryl-sulfatase, 3.1.6.3 glycosulfatase, 3.1.6.4 N-acetylgalactosamine-6-sulfatase, 3.1.6.5 sinigrin sulfohydrolase; myrosulfatase, 3.1.6.6 choline-sulfatase, 3.1.6.7 cellulose-polysulfatase, 3.1.6.8 cerebroside-sulfatase, 3.1.6.9 chondro-4-sulfatase, 3.1.6.10 chondro-6-sulfatase, 3.1.6.11 disulfoglucosamine-6-sulfatase, 3.1.6.12 N-acetylgalactosamine-4-sulfatase, 3.1.6.13 iduronate-2-sulfatase, 3.1.6.14 N-acetylglucosamine-6-sulfatase, 3.1.6.15 N-sulfoglucosamine-3-sulfatase, 3.1.6.16 monomethyl-sulfatase, 3.1.6.17 D-lactate-2-sulfatase, 3.1.6.18 glucuronate-2-sulfatase, 3.10.1.1 N-sulfoglucosamine sulfohydrolase, or combinations thereof.

Certain enzymes that are used in various embodiments of the methods described herein include, by way of non-limiting example, a deacetylase, e.g., an exo-deacetylase, including, by way of non-limiting example, the alpha-glucosaminide N-acetyltransferase (2.3.1.78) or similar enzymes.

Certain enzymes that are used in various embodiments of the methods described herein include, by way of non-limiting example, a carbohydrate phosphatase including, e.g., 3.1.3.1 alkaline phosphatase, 3.1.3.2 acid phosphatase, 3.1.3.B2 diacylglycerol pyrophosphate phosphatase, 3.1.3.3 phosphoserine phosphatase, 3.1.3.4 phosphatidate phosphatase, 3.1.3.5 5'-nucleotidase, 3.1.3.6 3'-nucleotidase, 3.1.3.7 3'(2'),5'-bisphosphate nucleotidase, 3.1.3.8 3-phytase, 3.1.3.9 glucose-6-phosphatase, 3.1.3.10 glucose-1-phosphatase, 3.1.3.11 fructose-bisphosphatase, 3.1.3.12 trehalose-phosphatase, 3.1.3.13 bisphosphoglycerate phosphatase, 3.1.3.14 methylphosphothioglycerate phosphatase, 3.1.3.15 histidinol-phosphatase, 3.1.3.16 phosphoprotein phosphatase, 3.1.3.17 [phosphorylase]phosphatase, 3.1.3.18 phosphoglycolate phosphatase, 3.1.3.19 glycerol-2-phosphatase, 3.1.3.20 phosphoglycerate phosphatase, 3.1.3.21 glycerol-1-phosphatase, 3.1.3.22 mannitol-1-phosphatase, 3.1.3.23 sugar-phosphatase, 3.1.3.24 sucrose-phosphate phosphatase, 3.1.3.25 inositol-phosphate phosphatase, 3.1.3.26 4-phytase, 3.1.3.27 phosphatidylglycerophosphatase, 3.1.3.28 ADP-phosphoglycerate phosphatase, 3.1.3.29 N-acylneuraminate-9-phosphatase, 3.1.3.30 3'-phosphoadenylylsulfate 3'-phosphatase, 3.1.3.31 nucleotidase, 3.1.3.32 polynucleotide 3'-phosphatase, 3.1.3.33 polynucleotide 5'-phosphatase, 3.1.3.34 deoxynucleotide 3'-phosphatase, 3.1.3.35 thymidylate 5'-phosphatase, 3.1.3.36 phosphoinositide 5-phosphatase, 3.1.3.37 sedoheptulose-bisphosphatase, 3.1.3.38 3-phosphoglycerate phosphatase, 3.1.3.39 streptomycin-6-phosphatase, 3.1.3.40 guanidinodeoxy-scyllo-inositol-4-phosphatase, 3.1.3.41 4-nitrophenylphosphatase, 3.1.3.42 [glycogen-synthase-D]phosphatase, 3.1.3.43 [pyruvate dehydrogenase (acetyl-transferring)]-phosphatase, 3.1.3.44 [acetyl-CoA carboxylase]-phosphatase, 3.1.3.45 3-deoxy-manno-octulosonate-8-phosphatase, 3.1.3.46 fructose-2,6-bisphosphate 2-phosphatase, 3.1.3.47 [hydroxymethylglutaryl-CoA reductase (NADPH)]-phosphatase, 3.1.3.48 protein-tyrosine-phosphatase, 3.1.3.49 [pyruvate kinase]-phosphatase, 3.1.3.50 sorbitol-6-phosphatase, 3.1.3.51 dolichyl-phosphatase, 3.1.3.52 [3-methyl-2-oxobutanoate dehydrogenase (2-methylpropanoyl-transferring)]-phosphatase, 3.1.3.53 [myosin-light-chain]phosphatase, 3.1.3.54 fructose-2,6-bisphosphate 6-phosphatase, 3.1.3.55 caldesmon-phosphatase, 3.1.3.56 inositol-polyphosphate 5-phosphatase, 3.1.3.57 inositol-1,4-bisphosphate 1-phosphatase, 3.1.3.58 sugar-terminal-phosphatase, 3.1.3.59 alkylacetylglycerophosphatase, 3.1.3.60 phosphoenolpyruvate phosphatase, 3.1.3.61 inositol-1,4,5-trisphosphate 1-phosphatase, 3.1.3.62 multiple inositol-polyphosphate phosphatase, 3.1.3.632-carboxy-D-arabinitol-1-phosphatase, 3.1.3.64 phosphatidylinositol-3-phosphatase, 3.1.3.65 inositol-1,3-bisphosphate 3-phosphatase, 3.1.3.66 phosphatidylinositol-3,4-bisphosphate 4-phosphatase, 3.1.3.67 phosphatidylinositol-3,4,5-trisphosphate 3-phosphatase, 3.1.3.68 2-deoxyglucose-6-phosphatase, 3.1.3.69 glucosylglycerol 3-phosphatase, 3.1.3.70 mannosyl-3-phosphoglycerate phosphatase, 3.1.3.71 2-phosphosulfolactate phosphatase, 3.1.3.72 5-phytase, 3.1.3.73 alpha-ribazole phosphatase, 3.1.3.74 pyridoxal phosphatase, 3.1.3.75 phosphoethanolamine/phosphocholine phosphatase, 3.1.3.76 lipid-phosphate phosphatase, 3.1.3.77 acireductone synthase, 3.1.3.78 phosphatidylinositol-4,5-bisphosphate 4-phosphatase, or 3.1.3.79 mannosylfructose-phosphate phosphatase, or a combination thereof.

In some embodiments, processes described herein include incubation and digestion with a first enzyme to clear a specific non-reducing end structure, incubation and digestion with a second enzyme. In certain embodiments, this multi-enzyme approach is useful in order to reduce the background. For example, in MPS II treating the sample with an iduronidase and/or glucuronidase to clear all non-sulfated non-reducing end uronic acids (this enzyme will not cleave sulfated iduronic acids) before 2-O sulfatase treatment. This approach will clear all non-sulfated non-reducing end uronic acids so that upon desulfation with the 2-O sulfatase the newly releasable uronic acids will be those that were previously sulfated (and therefore resistant to the action of the iduronidase and/or glucuronidase).

Glycan Residual Compounds:

Glycan residual compounds detected, measured, analyzed, and/or otherwise characterized according to any process described herein include any suitable glycan residue that is liberated from the non-reducing end of a glycan (e.g., a glycan obtained from a biological sample of an individual). In specific instances, glycan residual compounds including, e.g., oligosaccharides, monosaccharides, sulfate, phosphate, sialic acid, acetate, or the like.

Specific glycan residual compounds useful in any process herein are described in Tables 1-4.

In some embodiments, the generated biomarker is a glycan residual compound. In some embodiments, the glycan residual compound is a monosaccharide. In certain embodiments, the glycan residual compound is sulfate, phosphate, acetate, or a combination thereof. In certain embodiments, the glycan residual compound has a molecular weight of less than 2000 g/mol, less than 1500 g/mol, less than 1000 g/mol, less than 500 g/mol, less than 400 g/mol, less than 300 g/mol, less than 260 g/mol, less than 200 g/mol, less than 100 g/mol, or the like (e.g., prior to tagging with any detectable label that may be included in a process described herein).

Disorders:

In certain embodiments, a disorder associated with abnormal glycan accumulation includes a disorder associated therewith is caused by an abnormally functioning glycan degradation enzyme. In various embodiments, the abnormally functioning glycan degradation enzyme functions abnormally as a result of being present in an abnormally low amount, functioning improperly, or a combination thereof. For example, an abnormally functioning glycan degradation enzyme functions abnormally as a result of being present in an amount of less than 50%, less than 40%, less than 30%, less than 20%, less than 10%, or less than 5% than is present in an individual with normal amounts of the glycan degradation enzyme (e.g., an individual in a non-diseased, normal, or wild type state). In further or alternative embodiments, abnormally functioning glycan degradation enzymes are present in a normal amount, but do not function properly in degrading glycans. For example, such enzymes may be have amino acid substitutions in the sequences thereof that reduce or eliminate the glycan degradative properties of the enzyme.

MPS I is a human genetic disease caused by a deficiency in the lysosomal enzyme L-iduronidase. This enzyme is required in the lysosome to degrade glycans that contain iduronic acid. Due to this enzymatic deficiency, glycans with an iduronic acid on the non-reducing end accumulate to high levels (including heparan sulfate and dermatan sulfate). In certain embodiments, using the method described herein, MPS I is diagnosed in an individual from a biological sample taken therefrom. For example, in some embodiments, a biological sample is optionally placed into a defined MW cut off spin column (retains large molecules when spun), optionally washed (e.g., with water or buffer) to remove free monosaccharides, then treated with an iduronidase (e.g., to liberate a glycan residual compound iduronic acid). In certain embodiments, after incubation, the liberated iduronic acid is isolated, e.g., by washing the free monosaccharide through the defined MW cut off membrane (or other methods). In some of such embodiments, the monosaccharide would be in the flow through. The isolated monosaccharide solution is optionally dried or otherwise treated to concentrate the sample and subsequently analyzed for iduronic acid content by any suitable analytical technique (e.g., HPLC, MS, GC, or the like with or without chemical or enzymatic derivatization before detection). This method can be used to detect MPS I disease, measure disease severity, or to measure response to therapy.

MPS II is a human genetic disease caused by a deficiency in the lysosomal enzyme 2-sulfatase. This enzyme is required in the lysosome to degrade glycans that contain 2-O sulfated uronic acids. Due to this enzymatic deficiency, glycans with a 2-sulfated uronic acid on the non-reducing end accumulate to high levels (including heparan sulfate and dermatan sulfate). In certain embodiments, using the method described herein, MPS II is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 2-sulfatase (e.g., to liberate a glycan residual compound sulfate). In some embodiments, after incubation, the liberated sulfate is optionally isolated by washing the free monosaccharide (e.g., through a defined MW cut off membrane or by any other suitable method). In some of such embodiments, the free sulfate is in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS II disease, measure disease severity, or to measure response to therapy. In other exemplary embodiments, following treatment with a 2-sulfatase, the resulting 2-O desulfated non-reducing end uronic acid residues is optionally liberated with an iduronidase or glucuronidase. In some of such embodiments, the resulting liberated monosaccharide is optionally isolated, e.g., by washing free monosaccharide (e.g., through the defined MW cut off membrane or any other suitable method). In some of such embodiments, free iduronic or glucuronic acid is in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS II disease, measure disease severity, or to measure response to therapy.

MPS IIIA is a human genetic disease caused by a deficiency in the lysosomal enzyme N-sulfatase. This enzyme is required in the lysosome to degrade glycans that contain N-sulfated glucosamine residues. Due to this enzymatic deficiency, glycans with N-sulfated glucosamine residues on the non-reducing end accumulate to high levels (including heparan sulfate). In certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free sulfate, and treated with an N-sulfatase. In certain embodiments, after incubation, the liberated sulfate is optionally isolated, e.g., by washing the free monosaccharide (such as through a defined MW cut off membrane or any other suitable method). In some of such embodiments, free sulfate for detection and/or quantitation in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS IIIA disease, measure disease severity, or to measure response to therapy. In further or alternative embodiments, following treatment with an N-sulfatase, the resulting N-desulfated non-reducing end glucosamine residues is optionally liberated with a hexosaminidase. In some of such embodiments, liberated monosaccharide is optionally isolated (e.g., by washing the free monosaccharide, such as through the defined MW cut off membrane or any other suitable method). In some of such embodiments, free glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIIA disease, measure disease severity, or to measure response to therapy.

As discussed above, in certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free monosaccharide, and treated with an N-sulfo glucosaminidase such as a heparin lyase. In some embodiments, liberated sulfated monosaccharide is optionally isolated, e.g., by washing the free monosaccharide (such as through the defined MW cut off membrane or by any other suitable method). In some of such embodiments, free N-sulfated glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIIA disease, measure disease severity, or to measure response to therapy.

As discussed above, in certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free monosaccharide, and treated with an N-sulfatase. In certain embodiments, the resulting glycan is subsequently treated such that the N-desulfated non-reducing end glucosamine residues is acetylated (e.g., with an N-acetyl transferase) and subsequently liberated with a hexosaminidase. In some of such embodiments, the resulting liberated monosaccharide is optionally isolated, e.g., by washing the free monosaccharide (e.g., through a defined MW cut off membrane or any other suitable methods). In some of such embodiments, free N-acetyl glucosamine for detection and/or quantitation is present in the flow through. In certain embodiments, the resulting isolated composition is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIIA disease, measure disease severity, or to measure response to therapy.

MPS IIIB is a human genetic disease caused by a deficiency in the enzyme N-acetyl glucosaminidase. This enzyme is required in the lysosome to degrade glycans that contain N-acetyl glucosamine residues. Due to this enzymatic deficiency, glycans with a N-acetyl glucosamine residue on the non-reducing end accumulate to high levels (including heparan sulfate). In certain embodiments, using the method described herein, MPS IIIB is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free N-acetyl glucosamine), and treated with a-acetyl glucosaminidase or a heparin lyase (e.g., to liberate a glycan residual compound N-acetyl glucosamine). In some embodiments, after incubation, the liberated N-acetyl glucosamine is optionally isolated by washing the free monosaccharide (e.g., through a defined MW cut off membrane or by any other suitable method). In some of such embodiments, the free monosaccharide is in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIIB disease, measure disease severity, or to measure response to therapy.

As discussed above, in certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free acetate, and treated with a deacetylase. The liberated acetate is optionally isolated, e.g., by washing the free acetate (such as through the defined MW cut off membrane or any other suitable method). In some of such embodiments, the free acetate for detection and/or quantitation is present the flow through. In some embodiments, the resulting isolated solution is optionally dried or otherwise treated to concentrate the sample and subsequently analyzed for acetate content by any suitable analytical technique (e.g., HPLC, MS, GC, pH detection, or the like with or without chemical or enzymatic derivatization before detection). This method can be used to detect MPS IIIB disease, measure disease severity, or to measure response to therapy.

MPS IIIC is a human genetic disease caused by a deficiency in the enzyme N-acetyltransferase. This enzyme is required in the lysosome to degrade glycans that contain glucosamine residues. Due to this enzymatic deficiency, glycans with a glucosamine residue on the non-reducing end accumulate to high levels (including heparan sulfate). In certain embodiments, using the method described herein, MPS IIIC is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free glucosamine), and treated with a hexosaminidase or heparin lyase (e.g., to liberate a glycan residual compound glucosamine). In some embodiments, after incubation, the liberated glucosamine is optionally isolated by washing the free glucosamine (e.g., through a defined MW cut off membrane or by any other suitable method). In some of such embodiments, the free glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIIC disease, measure disease severity, or to measure response to therapy.

As discussed above, in certain embodiments, using the method described herein, MPS IIIC is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free glucosamine and/or N-acetyl glucosamine), and treated with a glucosamine N-acetyltransferase followed by a hexosaminidase (e.g., to liberate a glycan residual compound N-acetyl glucosamine). In some embodiments, after incubation, the liberated N-acetyl glucosamine is optionally isolated by washing the free N-acetyl glucosamine (e.g., through a defined MW cut off membrane or by any other suitable method). In some of such embodiments, the free N-acetyl glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIIC disease, measure disease severity, or to measure response to therapy.

MPS IIID is a human genetic disease caused by a deficiency in the enzyme glucosamine 6-0 sulfatase. This enzyme is required in the lysosome to degrade glycans that contain 6-O-sulfated glucosamine residues. Due to this enzymatic deficiency, glycans with a 6-O-sulfated N-acetyl glucosamine residue on the non-reducing end accumulate to high levels (including heparan sulfate). In certain embodiments, using the method described herein, MPS IIIC is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 6-O-sulfatase (e.g., to liberate a glycan residual compound sulfate). In some embodiments, after incubation, the liberated sulfate is optionally isolated by washing the free sulfate (e.g., through a defined MW cut off membrane or by any other suitable method). In some of such embodiments, the free sulfate for detection and/or quantitation is present in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS IIID disease, measure disease severity, or to measure response to therapy.

As discussed above, in certain embodiments, using the method described herein, MPS IIID is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate and/or N-acetyl glucosamine), and treated with a 6-O-sulfatase and a hexosaminidase (e.g., to liberate a glycan residual compound N-acetyl glucosamine). In some embodiments, after incubation, the liberated N-acetyl glucosamine is optionally isolated by washing the free N-acetyl glucosamine (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIID disease, measure disease severity, or to measure response to therapy.

As discussed above, in certain embodiments, using the method described herein, MPS IIID is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate and/or N-acetyl glucosamine 6-O sulfate), and treated with a hexosaminidase or heparin lyase (e.g., to liberate a glycan residual compound N-acetyl glucosamine 6-O sulfate). In some embodiments, after incubation, the liberated N-acetyl glucosamine 6-O sulfate is optionally isolated by washing the free N-acetyl glucosamine 6-O sulfate (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIID disease, measure disease severity, or to measure response to therapy.

MPS IVA is a human genetic disease caused by a deficiency in the enzyme lysosomal enzyme galactose/N-acetyl galactosamine 6-O sulfatase. This enzyme is required in the lysosome to degrade glycans that contain 6-O-sulfated galactose and 6-O sulfated N-acetyl galactosamine residues. Due to this enzymatic deficiency, glycans with 6-O-sulfated galactose and 6-O sulfated N-acetyl galactosamine residues on the non-reducing end accumulate to high levels (including chondroitin and keratan sulfate). In certain embodiments, using the method described herein, MPS IVA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharide), and treated with a galactose 6-O-sulfatase and/or an N-acetyl galactosamine 6-O sulfatase and a galactosidase and/or hexosaminidase (e.g., to liberate a glycan residual compound Gal and/or GalNAc). In some embodiments, after incubation, the liberated monosaccharide is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IVA disease, measure disease severity, or to measure response to therapy.

As discussed above, in certain embodiments, using the method described herein, MPS IVA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 6-O-sulfatase capable of desulfating 6-O-sulfated galactose and/or 6-O sulfated N-acetyl galactosamine residues (e.g., to liberate a glycan residual compound sulfate). In some embodiments, after incubation, the liberated sulfate is optionally isolated by washing the free sulfate (e.g., through a defined MW cut off membrane or by any other suitable method). In some of such embodiments, the free sulfate for detection and/or quantitation is present in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS IVA disease, measure disease severity, or to measure response to therapy.

MPS IVB is a human genetic disease caused by a deficiency in the enzyme lysosomal f3-galactosidase. This enzyme is required in the lysosome to degrade glycans that contain galactose residues. Due to this enzymatic deficiency, glycans with O-galactose residues on the non-reducing end accumulate to high levels (including keratan sulfate and other glycans). In certain embodiments, using the method described herein, MPS IVB is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharide), and treated with a galactosidase (e.g., to liberate a glycan residual compound Gal). In some embodiments, after incubation, the liberated monosaccharide is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IVB disease, measure disease severity, or to measure response to therapy.

MPS VI is a human genetic disease caused by a deficiency in the enzyme 4-0 sulfatase that desulfates N-acetyl galactosamine. This enzyme is required in the lysosome to degrade glycans that contain 4-O-sulfated N-acetyl galactosamine residues. Due to this enzymatic deficiency, glycans with 4-O-sulfated N-acetyl galactosamine residues on the non-reducing end accumulate to high levels (including chondroitin sulfate). In certain embodiments, using the method described herein, MPS VI is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 4-O-sulfatase that can desulfate 4-O-sulfated N-acetyl galactosamine residues (e.g., to liberate a glycan residual compound sulfate). In some embodiments, after incubation, the liberated sulfate is optionally isolated by washing the free sulfate (e.g., through a defined MW cut off membrane or by any other suitable method). In some of such embodiments, the free sulfate for detection and/or quantitation is present in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS VI disease, measure disease severity, or to measure response to therapy.

As discussed above, in certain embodiments, using the method described herein, MPS VI is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free N-acetyl galactosamine), and treated with a 4-O-sulfatase that is capable of desulfating 4-O-sulfated N-acetyl galactosamine residues then treated with a hexosaminidase (e.g., to liberate a glycan residual compound N-acetyl galactosamine). In some embodiments, after incubation, the liberated N-acetyl galactosamine is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS VI disease, measure disease severity, or to measure response to therapy.

MPS VII is a human genetic disease caused by a deficiency in the lysosomal enzyme beta-glucuronidase. This enzyme is required in the lysosome to degrade glycans that contain glucuronic acid residues. Due to this enzymatic deficiency, glycans with glucuronic acid residues on the non-reducing end accumulate to high levels (including chondroitin sulfate, heparan sulfate and others). In certain embodiments, using the method described herein, MPS VII is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free glucuronic acid), and treated with a glucuronidase (e.g., to liberate a glycan residual compound glucuronic acid). In some embodiments, after incubation, the liberated monosaccharide is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS VII disease, measure disease severity, or to measure response to therapy.

Methods described herein can also be used to define the relative presence of different glycan classes.

Fabry Disease is a human genetic disease caused by a deficiency in the lysosomal $\alpha$-galactosidase. Due to this enzymatic deficiency, glycans with non-reducing end terminal $\alpha$-galactose residues are abundant. In certain embodiments, using the method described herein, Fabry Disease is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharide), and treated with a galactosidase that is capable of liberating a non-reducing end monosaccharide (e.g., to liberate a glycan residual compound). In some embodiments, after incubation, the liberated glycan residual compound is optionally isolated by washing the free glycan residual compound (e.g., through a defined MW cut off membrane or by any other suitable method). In some of such embodiments, the free glycan residual compound for detection and/or quantitation is present in the flow through. In certain embodiments, the resulting isolated solution is optionally dried or otherwise treated to concentrate the sample and subsequently analyzed for glycan residual compound content by any suitable analytical technique (e.g., HPLC, MS, GC, pH detection, or the like with or without chemical or enzymatic derivatization before detection). This method can be used to detect Fabry Disease, measure disease severity, or to measure response to therapy.

In some embodiments, as described in Table 1, other enzymes and processes are optionally utilized to diagnose other lysosomal storage diseases (LSDs). As described in the table, the appropriate enzyme(s) can be selected as appropriate for the specific disease.

Oncology—Melanoma and Neuroblastoma via Sialic Acid

A hallmark of cancer is altered glycosylation. The changes in glycosylation are a reflection of changes in enzymes and factors that regulate the biosynthesis, turnover, presentation, stability, solubility, and degradation of glycans. Many of these changes result in glycans being produced that have altered structures. The methods described here are utilized in various embodiments to evaluate those structural changes (e.g., measure abnormal glycan accumulation) that are present on the non-reducing end of the glycans present in individuals suffering from a cancerous disease.

Some examples of cancerous diseases suitable for diagnosis and/or monitoring therapy according to methods described herein include, by way of non-limiting example, melanoma and neuroblastoma. In some instances, such cancers have alterations in the biosynthesis, turnover, presentation, stability, solubility, or degradation of gangliosides. In some instances, these sialic acid modified glycolipids are detected and/or otherwise characterized or analyzed in a biological sample (e.g., serum) of patients with these tumor types. In some embodiments, the abundance of the heterogeneous population of gangliosides is quantified to measuring sialic acid or other glycan residual released from gangliosides in the blood.

Due to this enzymatic alteration, gangliosides and other glycans are present in the body at high levels. In certain embodiments, using the method described herein, cancer (e.g., melanoma or neuroblastoma) is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sialic acid), and treated with a sialidase that can liberate sialic acid (e.g., to liberate a glycan residual compound sialic acid). In some embodiments, after incubation, the liberated sialic acid is optionally isolated by washing the free sialic acid (e.g., through a defined MW cut off membrane or by any other suitable method). In some of such embodiments, the free sialic acid for detection and/or quantitation is present in the flow through. In certain embodiments, the resulting isolated solution is optionally dried or otherwise treated to concentrate the sample and subsequently analyzed for sialic acid content by any suitable analytical technique (e.g., HPLC, MS, GC, pH detection, or the like with or without chemical or enzymatic derivatization before detection). This method can be used to detect cancer (e.g., melanoma or neuroblastoma) disease, measure disease severity, or to measure response to therapy.

Oncology—Myeloma via Heparan Sulfate Nonreducing Ends

An example of a human cancer that is diagnosed and/or monitored according to the methods described herein (i.e., by analyzing with such a method the altered degradation of a glycan) is multiple myeloma. In certain instances, multiple myeloma commonly produces heparanase. Heparanase is an endoglycosidase that cleaved heparan sulfate into smaller fragments, exposing novel non-reducing end structures. In certain embodiments described herein, the presence of these novel non-reducing end structures are detected using any method described herein (e.g., by incubating a biological sample with various glycosidases or sulfatases to detect the presence of novel glycan non-reducing ends).

Due to this enzymatic alteration, glycans (including heparan sulfate and others) are present in the body at high levels. In certain embodiments, using the method described herein, cancer (e.g., multiple myeloma) is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharides and/or sulfate), and treated with a sulfatase, iduronidase, glucuronidase, hexosaminidase, or lyase that is capable of liberating a non-reducing end monosaccharide or sulfate. In some embodiments, after incubation, the liberated glycan residual compound is optionally isolated by washing the free glycan residual compound (e.g., through a defined MW cut off membrane or by any other suitable method). In some of such embodiments, the free glycan residual compound for detection and/or quantitation is present in the flow through. In certain embodiments, the resulting isolated solution is optionally dried or otherwise treated to concentrate the sample and subsequently analyzed for glycan residual compound content by any suitable analytical technique (e.g., HPLC, MS, GC, pH detection, or the like with or without chemical or enzymatic derivatization before detection). This method can be used to detect cancer (e.g., multiple myeloma) disease, measure disease severity, or to measure response to therapy.

Oncology—Adenocarcinoma

Adenocarcinoma is associated with changes in glycosylation including increased sialylation and fucosylation. The described method can be used to measure disease by analyzing glycans (total or purified or enriched for specific glycan classes) from a patient for the amount of nonreducing end terminal sialic acid or fucose, by measuring the release of these glycan residuals after treatment with a sialidase or fucosidase.

Other Applications

As described in Tables 1-4, various diseases associated with changes in glycosylation are optionally diagnosed and/or monitored according to methods described herein. Various disorders include, by way of non-limiting example, lysosomal storage disease, cancer, neurological disease (dementia, Alzheimer's, etc), liver disease, bone disease, infectious diseases, and the like.

Provided herein are methods of diagnosing individuals (including, e.g., a disease state or the severity of a disease states) with a lysosomal storage disease (LSD) or methods of monitoring the treatment of a lysosomal storage disease (LSD). Provided in Table 1 are specific embodiments of disease that are optionally diagnosed and/or monitored according to various embodiments described herein. Table 1 also illustrates various non-limiting embodiments of specific enzyme(s) that are optionally utilized to treat a biological sample from an individual suffering from or suspected (e.g., through a pre- or preliminary screening process) of suffering from an LSD. Moreover, Table 1 further illustrates various glycan residual compounds that are liberated in various embodiments described herein, such liberated glycan residual compounds optionally being detected and/or measured in order to diagnose and/or monitor a lysosomal storage disease (LSD).

TABLE 1

Exemplary LSD Uses

| Disease | Non-Reducing End Structure | Primary Releasing Enzyme | Secondary Releasing Enzyme | Glycan Residual Compound |
|---|---|---|---|---|
| MPS I | IdoA | iduronidase | | IdoA |
| MPS II | IdoA-2-O sufate and GlcA-2-O sufate | 2-sulfatase | | Sulfate |
| MPS II | IdoA-2-O sufate and GlcA-2-O sufate | 2-sulfatase | Iduronidase and/or glucuronidase | IdoA and/or GlcA |
| MPS IIIA | GlcN-N-sulfate | N-sulfatase | | Sulfate |
| MPS IIIA | GlcN-N-sulfate | N-sulfatase | hexosaminidase | GlcN |
| MPS IIIA | GlcN-N-sulfate | N-sulfatase | Heparin lyase | GlcN |
| MPS IIIA | GlcN-N-sulfate | N-sulfatase | N-acetyl transferase and hexosaminidase | GlcNAc |
| MPS IIIA | GlcN-N-sulfate | Heparin lyase | | GlcN-N-sulfate |
| MPS IIIB | GlcNAc | hexosaminidase | | GlcNAc |
| MPS IIIB | GlcNAc | Deacetylase | | acetate |
| MPS IIIB | GlcNAc | Heparin lyase | | GlcNAc |
| MPS IIIC | GlcNAc-6-O sulfate | 6-O sulfatase | | Sulfate |
| MPS IIIC | GlcNAc-6-O sulfate | 6-O sulfatase | hexosaminidase | GlcNAc |
| MPS IIIC | GlcNAc-6-O sulfate | 6-O sulfatase | Heparin lyase | GlcNAc |
| MPS IIIC | GlcNAc-6-O sulfate | Heparin lyase | | GlcNAc-6-O sulfate |
| MPS IIID | GlcN | hexosaminidase | | GlcN |
| MPS IIID | GlcN | Heparin lyase | | GlcN |
| MPS IIID | GlcN | N-acetyl transferase | hexosaminidase | GlcNAc |
| MPS IVA | Gal-6-O sulfate and GalNAc-6-O sulfate | 6-O sulfatase | | Sulfate |
| MPS IVA | Gal-6-O sulfate and GalNAc-6-O sulfate | galactosidase | | Gal-6-O sulfate |
| MPS IVA | Gal-6-O sulfate and GalNAc-6-O sulfate | N-acetyl galactosidase | | GalNAc-6-O sulfate |
| MPS IVA | Gal-6-O sulfate and GalNAc-6-O sulfate | hexosaminidase | | GalNAc-6-O sulfate |
| MPS IVA | Gal-6-O sulfate and GalNAc-6-O sulfate | 6-O sulfatase | galactosidase | Gal |
| MPS IVA | Gal-6-O sulfate and GalNAc-6-O sulfate | 6-O sulfatase | N-acetyl galactosidase | GalNAc |
| MPS IVB | Gal | Galactosidase | | Gal |
| MPS VI | GalNAc-4-O sulfate | 4-O sulfatase | | Sulfate |
| MPS VI | GalNAc-4-O sulfate | 4-O sulfatase | hexosaminidase | GalNAc |
| MPS VI | GalNAc-4-O sulfate | 4-O sulfatase | Chondroitin lyase | GalNAc |
| MPS VI | GalNAc-4-O sulfate | Chondroitin lyase | | GalNAc-4-O sulfate |
| MPS VII | GlcA | β-glucuronidase | | GlcA |
| Alpha Mannosidosis | Mannose | Manosidase | | Man |
| Aspartylglucosaminuria | GlcNAc | hexosaminidase | | GlcNAc |
| Fabry | Galactose | galactosidase | | Gal |
| Fucosidosis | Fucose | fucosidase | | Fuc |
| Galactosialidosis | Galactose and/or Sialic acid | Galactosidase and/or sialidase | | Gal and/or Sialic acid |
| Gaucher | glucose | glucosidase | | glucose |
| GM1 gangliosidosis | Beta-Galactose | Beta-Galactosidase | | Beta-galactose |
| GM1 gangliosidosis | Beta-Galactose | Beta-Galactosidase | Hexosaminidase | GalNAc |
| GM2 activator deficiency | GalNAc | hexosaminidase | | GalNAc |
| Sialidosis | Sialic acid | Sialidase | | Sialic acid |
| Sialidosis | Sialic acid | Alpha 2,3 Sialidase | | Sialic acid |

TABLE 1-continued

Exemplary LSD Uses

| Disease | Non-Reducing End Structure | Primary Releasing Enzyme | Secondary Releasing Enzyme | Glycan Residual Compound |
|---|---|---|---|---|
| Sialidosis | Sialic acid | Alphas 2,6 Sialidase | | Sialic acid |
| Sialidosis | Sialic acid | Alphas 2,8 Sialidase | | Sialic acid |
| Krabbe | Galactose | galactosidase | | Galactose |
| Metachromatic Leukodystrophy | Sulfated galactosylceramide | 3-O sulfatase | | Sulfate |
| Metachromatic Leukodystrophy | Sulfated galactosylceramide | 3-O sulfatase | galactosidase | Galactose |
| Mucolipidosis II | Broad range of glycans | Any listed enzyme | | Any monosaccharide or sulfate |
| Mucolipidosis III | Broad range of glycans | Any listed enzyme | | Any monosaccharide or sulfate |
| Mucolipidosis IV | Broad range of glycans | Any listed enzyme | | Any monosaccharide or sulfate |
| Multiple Sulfatase Deficiency | Sulfated glycans | sulfatase | | sulfate |
| Multiple Sulfatase Deficiency | Sulfated glycans | sulfatase | Any glycosidase | monosaccharide |
| Multiple Sulfatase Deficiency | Sulfated glycans | Any glycosidase | | Sulfated monosaccharide |
| Glycogen Storage Disease (Pompe) | glucose | glucosidase | | glucose |
| Sandhoff | GalNAc | hexosaminidase | | GalNAc |
| Tay-Sachs | GalNAc | hexosaminidase | | GalNAc |
| AB Variant | GalNAc | hexosaminidase | | GalNAc |
| Schindler Disease | Alpha-GalNAc | hexosaminidase | | GalNAc |
| Salla Disease | Sialic acid | none | | Sialic Acid |
| Alpha Mannosidosis | Alpha mannose | mannosidase | | Mannose |
| Beta Mannosidosis | Beta mannose | mannosidase | | Mannose |
| Globoid cell leukodystrophy | galactose | galactosidase | | galactose |

Provided herein are methods of diagnosing individuals (including, e.g., a disease state or the severity of a disease states) with a cancerous disease state or methods of monitoring the treatment of a cancer. Provided in Table 2 are specific embodiments of disease that are optionally diagnosed and/or monitored according to various embodiments described herein. Table 2 also illustrates various non-limiting embodiments of specific enzyme(s) that are optionally utilized to treat a biological sample from an individual suffering from or suspected of (e.g., through a pre- or preliminary screening process) suffering from a cancerous disease state. Moreover, Table 2 further illustrates various glycan residual compounds that are liberated in various embodiments described herein, such liberated glycan residual compounds optionally being detected and/or measured in order to diagnose and/or monitor a cancerous disease state.

TABLE 2

Exemplary Oncology Uses

| Cancer Type | Non-Reducing End Structure | Primary Liberating Enzyme | Secondary Liberating Enzyme | Glycan Residual Compound |
|---|---|---|---|---|
| Melanoma | Sialic Acid | Sialidase | | Sialic acid |
| Melanoma | Sialic Acid | Alpha 2,8 Sialidase | | Sialic acid |
| Melanoma | Sialic Acid | Alpha 2,3 Sialidase | | Sialic acid |
| Melanoma | Sialic Acid | Alpha 2,6 Sialidase | | Sialic acid |
| Melanoma | GalNAc | Hexosaminidase | | GalNAc |
| Melanoma | GalNAc | Sialidase | Hexosaminidase | GalNAc |
| Melanoma | Sialic acid | Hexosaminidase | Sialidase | Sialic acid |
| Melanoma | Galactose | galactosidase | | Galactose |
| Melanoma | Galactose | sialidase | galactosidase | Galactose |
| Melanoma | Fucose | fucosidase | | Fucose |
| Melanoma | Galactose | Galactosidase | | Galactose |
| Melanoma | GlcNAc | hexosaminidase | | GlcNAc |

TABLE 2-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Melanoma | Sulfate | Sulfatase | | Sulfate |
| Melanoma | Sulfated hexose | Sulfatase | hexosaminidase | GlcNAc or GalNAc |
| Melanoma | Sulfated uronic acid | Sulfatase | Iduronidase or glucouronidase | IdoA or GlcA |
| Neuroblastoma | Sialic Acid | Sialidase | | Sialic acid |
| Neuroblastoma | Sialic Acid | Alpha 2,8 Sialidase | | Sialic acid |
| Neuroblastoma | Sialic Acid | Alpha 2,3 Sialidase | | Sialic acid |
| Neuroblastoma | Sialic Acid | Alpha 2,6 Sialidase | | Sialic acid |
| Neuroblastoma | GalNAc | Hexosaminidase | | GalNAc |
| Neuroblastoma | GalNAc | Sialidase | Hexosaminidase | GalNAc |
| Neuroblastoma | Sialic acid | Hexosaminidase | Sialidase | Sialic acid |
| Neuroblastoma | Galactose | galactosidase | | Galactose |
| Neuroblastoma | Galactose | sialidase | galactosidase | Galactose |
| Neuroblastoma | Fucose | fucosidase | | Fucose |
| Neuroblastoma | Galactose | Galactosidase | | Galactose |
| Neuroblastoma | GlcNAc | hexosaminidase | | GlcNAc |
| Neuroblastoma | Sulfate | Sulfatase | | Sulfate |
| Neuroblastoma | Sulfated hexose | Sulfatase | hexosaminidase | GlcNAc or GalNAc |
| Neuroblastoma | Sulfated uronic acid | Sulfatase | Iduronidase or glucouronidase | IdoA or GlcA |
| Adenocarcinoma | Sialic Acid | Sialidase | | Sialic acid |
| Adenocarcinoma | Sialic Acid | Alpha 2,8 Sialidase | | Sialic acid |
| Adenocarcinoma | Sialic Acid | Alpha 2,3 Sialidase | | Sialic acid |
| Adenocarcinoma | Sialic Acid | Alpha 2,6 Sialidase | | Sialic acid |
| Adenocarcinoma | GalNAc | Hexosaminidase | | GalNAc |
| Adenocarcinoma | GalNAc | Sialidase | Hexosaminidase | GalNAc |
| Adenocarcinoma | Sialic acid | Hexosaminidase | Sialidase | Sialic acid |
| Adenocarcinoma | Galactose | galactosidase | | Galactose |
| Adenocarcinoma | Galactose | sialidase | galactosidase | Galactose |
| Adenocarcinoma | Fucose | fucosidase | | Fucose |
| Adenocarcinoma | Galactose | Galactosidase | | Galactose |
| Adenocarcinoma | GlcNAc | hexosaminidase | | GlcNAc |
| Adenocarcinoma | Sulfate | Sulfatase | | Sulfate |
| Adenocarcinoma | Sulfated hexose | Sulfatase | hexosaminidase | GlcNAc or GalNAc |
| Adenocarcinoma | Sulfated uronic acid | Sulfatase | Iduronidase or glucouronidase | IdoA or GlcA |
| Myeloma | Sialic Acid | Sialidase | | Sialic acid |
| Myeloma | Sialic Acid | Alpha 2,8 Sialidase | | Sialic acid |
| Myeloma | Sialic Acid | Alpha 2,3 Sialidase | | Sialic acid |
| Myeloma | Sialic Acid | Alpha 2,6 Sialidase | | Sialic acid |
| Myeloma | GalNAc | Hexosaminidase | | GalNAc |
| Myeloma | GalNAc | Sialidase | Hexosaminidase | GalNAc |
| Myeloma | Sialic acid | Hexosaminidase | Sialidase | Sialic acid |
| Myeloma | Galactose | galactosidase | | Galactose |
| Myeloma | Galactose | sialidase | galactosidase | Galactose |
| Myeloma | Fucose | fucosidase | | Fucose |
| Myeloma | Galactose | Galactosidase | | Galactose |
| Myeloma | GlcNAc | hexosaminidase | | GlcNAc |
| Myeloma | Sulfate | Sulfatase | | Sulfate |
| Myeloma | Sulfated hexose | Sulfatase | hexosaminidase | GlcNAc or GalNAc |
| Myeloma | Sulfated uronic acid | Sulfatase | Iduronidase or glucouronidase | IdoA or GlcA |
| Breast | Sialic Acid | Sialidase | | Sialic acid |
| Breast | Sialic Acid | Alpha 2,8 Sialidase | | Sialic acid |
| Breast | Sialic Acid | Alpha 2,3 Sialidase | | Sialic acid |
| Breast | Sialic Acid | Alpha 2,6 Sialidase | | Sialic acid |
| Breast | GalNAc | Hexosaminidase | | GalNAc |
| Breast | GalNAc | Sialidase | Hexosaminidase | GalNAc |
| Breast | Sialic acid | Hexosaminidase | Sialidase | Sialic acid |
| Breast | Galactose | galactosidase | | Galactose |
| Breast | Galactose | sialidase | galactosidase | Galactose |
| Breast | Fucose | fucosidase | | Fucose |
| Breast | Galactose | Galactosidase | | Galactose |
| Breast | GlcNAc | hexosaminidase | | GlcNAc |
| Breast | Sulfate | Sulfatase | | Sulfate |

TABLE 2-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Breast | Sulfated hexose | Sulfatase | hexosaminidase | GlcNAc or GalNAc |
| Breast | Sulfated uronic acid | Sulfatase | Iduronidase or glucouronidase | IdoA or GlcA |
| Ovarian | Sialic Acid | Sialidase | | Sialic acid |
| Ovarian | Sialic Acid | Alpha 2,8 Sialidase | | Sialic acid |
| Ovarian | Sialic Acid | Alpha 2,3 Sialidase | | Sialic acid |
| Ovarian | Sialic Acid | Alpha 2,6 Sialidase | | Sialic acid |
| Ovarian | GalNAc | Hexosaminidase | | GalNAc |
| Ovarian | GalNAc | Sialidase | Hexosaminidase | GalNAc |
| Ovarian | Sialic acid | Hexosaminidase | Sialidase | Sialic acid |
| Ovarian | Galactose | galactosidase | | Galactose |
| Ovarian | Galactose | sialidase | galactosidase | Galactose |
| Ovarian | Fucose | fucosidase | | Fucose |
| Ovarian | Galactose | Galactosidase | | Galactose |
| Ovarian | GlcNAc | hexosaminidase | | GlcNAc |
| Ovarian | Sulfate | Sulfatase | | Sulfate |
| Ovarian | Sulfated hexose | Sulfatase | hexosaminidase | GlcNAc or GalNAc |
| Ovarian | Sulfated uronic acid | Sulfatase | Iduronidase or glucouronidase | IdoA or GlcA |
| Stomach | Sialic Acid | Sialidase | | Sialic acid |
| Stomach | Sialic Acid | Alpha 2,8 Sialidase | | Sialic acid |
| Stomach | Sialic Acid | Alpha 2,3 Sialidase | | Sialic acid |
| Stomach | Sialic Acid | Alpha 2,6 Sialidase | | Sialic acid |
| Stomach | GalNAc | Hexosaminidase | | GalNAc |
| Stomach | GalNAc | Sialidase | Hexosaminidase | GalNAc |
| Stomach | Sialic acid | Hexosaminidase | Sialidase | Sialic acid |
| Stomach | Galactose | galactosidase | | Galactose |
| Stomach | Galactose | sialidase | galactosidase | Galactose |
| Stomach | Fucose | fucosidase | | Fucose |
| Stomach | Galactose | Galactosidase | | Galactose |
| Stomach | GlcNAc | hexosaminidase | | GlcNAc |
| Stomach | Sulfate | Sulfatase | | Sulfate |
| Stomach | Sulfated hexose | Sulfatase | hexosaminidase | GlcNAc or GalNAc |
| Stomach | Sulfated uronic acid | Sulfatase | Iduronidase or glucouronidase | IdoA or GlcA |
| Lung | Sialic Acid | Sialidase | | Sialic acid |
| Lung | Sialic Acid | Alpha 2,8 Sialidase | | Sialic acid |
| Lung | Sialic Acid | Alpha 2,3 Sialidase | | Sialic acid |
| Lung | Sialic Acid | Alpha 2,6 Sialidase | | Sialic acid |
| Lung | GalNAc | Hexosaminidase | | GalNAc |
| Lung | GalNAc | Sialidase | Hexosaminidase | GalNAc |
| Lung | Sialic acid | Hexosaminidase | Sialidase | Sialic acid |
| Lung | Galactose | galactosidase | | Galactose |
| Lung | Galactose | sialidase | galactosidase | Galactose |
| Lung | Fucose | fucosidase | | Fucose |
| Lung | Galactose | Galactosidase | | Galactose |
| Lung | GlcNAc | hexosaminidase | | GlcNAc |
| Lung | Sulfate | Sulfatase | | Sulfate |
| Lung | Sulfated hexose | Sulfatase | hexosaminidase | GlcNAc or GalNAc |
| Lung | Sulfated uronic acid | Sulfatase | Iduronidase or glucouronidase | IdoA or GlcA |
| Pancreatic | Sialic Acid | Sialidase | | Sialic acid |
| Pancreatic | Sialic Acid | Alpha 2,8 Sialidase | | Sialic acid |
| Pancreatic | Sialic Acid | Alpha 2,3 Sialidase | | Sialic acid |
| Pancreatic | Sialic Acid | Alpha 2,6 Sialidase | | Sialic acid |
| Pancreatic | GalNAc | Hexosaminidase | | GalNAc |
| Pancreatic | GalNAc | Sialidase | Hexosaminidase | GalNAc |
| Pancreatic | Sialic acid | Hexosaminidase | Sialidase | Sialic acid |
| Pancreatic | Galactose | galactosidase | | Galactose |
| Pancreatic | Galactose | sialidase | galactosidase | Galactose |
| Pancreatic | Fucose | fucosidase | | Fucose |
| Pancreatic | Galactose | Galactosidase | | Galactose |
| Pancreatic | GlcNAc | hexosaminidase | | GlcNAc |

TABLE 2-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Pancreatic | Sulfate | Sulfatase | | Sulfate |
| Pancreatic | Sulfated hexose | Sulfatase | hexosaminidase | GlcNAc or GalNAc |
| Pancreatic | Sulfated uronic acid | Sulfatase | Iduronidase or glucouronidase | IdoA or GlcA |
| Oral | Sialic Acid | Sialidase | | Sialic acid |
| Oral | Sialic Acid | Alpha 2,8 Sialidase | | Sialic acid |
| Oral | Sialic Acid | Alpha 2,3 Sialidase | | Sialic acid |
| Oral | Sialic Acid | Alpha 2,6 Sialidase | | Sialic acid |
| Oral | GalNAc | Hexosaminidase | | GalNAc |
| Oral | GalNAc | Sialidase | Hexosaminidase | GalNAc |
| Oral | Sialic acid | Hexosaminidase | Sialidase | Sialic acid |
| Oral | Galactose | galactosidase | | Galactose |
| Oral | Galactose | sialidase | galactosidase | Galactose |
| Oral | Fucose | fucosidase | | Fucose |
| Oral | Galactose | Galactosidase | | Galactose |
| Oral | GlcNAc | hexosaminidase | | GlcNAc |
| Oral | Sulfate | Sulfatase | | Sulfate |
| Oral | Sulfated hexose | Sulfatase | hexosaminidase | GlcNAc or GalNAc |
| Oral | Sulfated uronic acid | Sulfatase | Iduronidase or glucouronidase | IdoA or GlcA |
| Colorectal | Sialic Acid | Sialidase | | Sialic acid |
| Colorectal | Sialic Acid | Alpha 2,8 Sialidase | | Sialic acid |
| Colorectal | Sialic Acid | Alpha 2,3 Sialidase | | Sialic acid |
| Colorectal | Sialic Acid | Alpha 2,6 Sialidase | | Sialic acid |
| Colorectal | GalNAc | Hexosaminidase | | GalNAc |
| Colorectal | GalNAc | Sialidase | Hexosaminidase | GalNAc |
| Colorectal | Sialic acid | Hexosaminidase | Sialidase | Sialic acid |
| Colorectal | Galactose | galactosidase | | Galactose |
| Colorectal | Galactose | sialidase | galactosidase | Galactose |
| Colorectal | Fucose | fucosidase | | Fucose |
| Colorectal | Galactose | Galactosidase | | Galactose |
| Colorectal | GlcNAc | hexosaminidase | | GlcNAc |
| Colorectal | Sulfate | Sulfatase | | Sulfate |
| Colorectal | Sulfated hexose | Sulfatase | hexosaminidase | GlcNAc or GalNAc |
| Colorectal | Sulfated uronic acid | Sulfatase | Iduronidase or glucouronidase | IdoA or GlcA |
| Kidney | Sialic Acid | Sialidase | | Sialic acid |
| Kidney | Sialic Acid | Alpha 2,8 Sialidase | | Sialic acid |
| Kidney | Sialic Acid | Alpha 2,3 Sialidase | | Sialic acid |
| Kidney | Sialic Acid | Alpha 2,6 Sialidase | | Sialic acid |
| Kidney | GalNAc | Hexosaminidase | | GalNAc |
| Kidney | GalNAc | Sialidase | Hexosaminidase | GalNAc |
| Kidney | Sialic acid | Hexosaminidase | Sialidase | Sialic acid |
| Kidney | Galactose | galactosidase | | Galactose |
| Kidney | Galactose | sialidase | galactosidase | Galactose |
| Kidney | Fucose | fucosidase | | Fucose |
| Kidney | Galactose | Galactosidase | | Galactose |
| Kidney | GlcNAc | hexosaminidase | | GlcNAc |
| Kidney | Sulfate | Sulfatase | | Sulfate |
| Kidney | Sulfated hexose | Sulfatase | hexosaminidase | GlcNAc or GalNAc |
| Kidney | Sulfated uronic acid | Sulfatase | Iduronidase or glucouronidase | IdoA or GlcA |
| Bladder | Sialic Acid | Sialidase | | Sialic acid |
| Bladder | Sialic Acid | Alpha 2,8 Sialidase | | Sialic acid |
| Bladder | Sialic Acid | Alpha 2,3 Sialidase | | Sialic acid |
| Bladder | Sialic Acid | Alpha 2,6 Sialidase | | Sialic acid |
| Bladder | GalNAc | Hexosaminidase | | GalNAc |
| Bladder | GalNAc | Sialidase | Hexosaminidase | GalNAc |
| Bladder | Sialic acid | Hexosaminidase | Sialidase | Sialic acid |
| Bladder | Galactose | galactosidase | | Galactose |
| Bladder | Galactose | sialidase | galactosidase | Galactose |
| Bladder | Fucose | fucosidase | | Fucose |
| Bladder | Galactose | Galactosidase | | Galactose |
| Bladder | GlcNAc | hexosaminidase | | GlcNAc |
| Bladder | Sulfate | Sulfatase | | Sulfate |

TABLE 2-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Bladder | Sulfated hexose | Sulfatase | hexosaminidase | GlcNAc or GalNAc |
| Bladder | Sulfated uronic acid | Sulfatase | Iduronidase or glucouronidase | IdoA or GlcA |
| Prostate | Sialic Acid | Sialidase | | Sialic acid |
| Prostate | Sialic Acid | Alpha 2,8 Sialidase | | Sialic acid |
| Prostate | Sialic Acid | Alpha 2,3 Sialidase | | Sialic acid |
| Prostate | Sialic Acid | Alpha 2,6 Sialidase | | Sialic acid |
| Prostate | GalNAc | Hexosaminidase | | GalNAc |
| Prostate | GalNAc | Sialidase | Hexosaminidase | GalNAc |
| Prostate | Sialic acid | Hexosaminidase | Sialidase | Sialic acid |
| Prostate | Galactose | galactosidase | | Galactose |
| Prostate | Galactose | sialidase | galactosidase | Galactose |
| Prostate | Fucose | fucosidase | | Fucose |
| Prostate | Galactose | Galactosidase | | Galactose |
| Prostate | GlcNAc | hexosaminidase | | GlcNAc |
| Prostate | Sulfate | Sulfatase | | Sulfate |
| Prostate | Sulfated hexose | Sulfatase | hexosaminidase | GlcNAc or GalNAc |
| Prostate | Sulfated uronic acid | Sulfatase | Iduronidase or glucouronidase | IdoA or GlcA |
| Uterine | Sialic Acid | Sialidase | | Sialic acid |
| Uterine | Sialic Acid | Alpha 2,8 Sialidase | | Sialic acid |
| Uterine | Sialic Acid | Alpha 2,3 Sialidase | | Sialic acid |
| Uterine | Sialic Acid | Alpha 2,6 Sialidase | | Sialic acid |
| Uterine | GalNAc | Hexosaminidase | | GalNAc |
| Uterine | GalNAc | Sialidase | Hexosaminidase | GalNAc |
| Uterine | Sialic acid | Hexosaminidase | Sialidase | Sialic acid |
| Uterine | Galactose | galactosidase | | Galactose |
| Uterine | Galactose | sialidase | galactosidase | Galactose |
| Uterine | Fucose | fucosidase | | Fucose |
| Uterine | Galactose | Galactosidase | | Galactose |
| Uterine | GlcNAc | hexosaminidase | | GlcNAc |
| Uterine | Sulfate | Sulfatase | | Sulfate |
| Uterine | Sulfated hexose | Sulfatase | hexosaminidase | GlcNAc or GalNAc |
| Uterine | Sulfated uronic acid | Sulfatase | Iduronidase or glucouronidase | IdoA or GlcA |
| Thyroid | Sialic Acid | Sialidase | | Sialic acid |
| Thyroid | Sialic Acid | Alpha 2,8 Sialidase | | Sialic acid |
| Thyroid | Sialic Acid | Alpha 2,3 Sialidase | | Sialic acid |
| Thyroid | Sialic Acid | Alpha 2,6 Sialidase | | Sialic acid |
| Thyroid | GalNAc | Hexosaminidase | | GalNAc |
| Thyroid | GalNAc | Sialidase | Hexosaminidase | GalNAc |
| Thyroid | Sialic acid | Hexosaminidase | Sialidase | Sialic acid |
| Thyroid | Galactose | galactosidase | | Galactose |
| Thyroid | Galactose | sialidase | galactosidase | Galactose |
| Thyroid | Fucose | fucosidase | | Fucose |
| Thyroid | Galactose | Galactosidase | | Galactose |
| Thyroid | GlcNAc | hexosaminidase | | GlcNAc |
| Thyroid | Sulfate | Sulfatase | | Sulfate |
| Thyroid | Sulfated hexose | Sulfatase | hexosaminidase | GlcNAc or GalNAc |
| Thyroid | Sulfated uronic acid | Sulfatase | Iduronidase or glucouronidase | IdoA or GlcA |
| Liver | Sialic Acid | Sialidase | | Sialic acid |
| Liver | Sialic Acid | Alpha 2,8 Sialidase | | Sialic acid |
| Liver | Sialic Acid | Alpha 2,3 Sialidase | | Sialic acid |
| Liver | Sialic Acid | Alpha 2,6 Sialidase | | Sialic acid |
| Liver | GalNAc | Hexosaminidase | | GalNAc |
| Liver | GalNAc | Sialidase | Hexosaminidase | GalNAc |
| Liver | Sialic acid | Hexosaminidase | Sialidase | Sialic acid |
| Liver | Galactose | galactosidase | | Galactose |
| Liver | Galactose | sialidase | galactosidase | Galactose |
| Liver | Fucose | fucosidase | | Fucose |

TABLE 2-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Liver | Galactose | Galactosidase | | Galactose |
| Liver | GlcNAc | hexosaminidase | | GlcNAc |
| Liver | Sulfate | Sulfatase | | Sulfate |
| Liver | Sulfated hexose | Sulfatase | hexosaminidase | GlcNAc or GalNAc |
| Liver | Sulfated uronic acid | Sulfatase | Iduronidase or glucouronidase | IdoA or GlcA |
| Esophagus | Sialic Acid | Sialidase | | Sialic acid |
| Esophagus | Sialic Acid | Alpha 2,8 Sialidase | | Sialic acid |
| Esophagus | Sialic Acid | Alpha 2,3 Sialidase | | Sialic acid |
| Esophagus | Sialic Acid | Alpha 2,6 Sialidase | | Sialic acid |
| Esophagus | GalNAc | Hexosaminidase | | GalNAc |
| Esophagus | GalNAc | Sialidase | Hexosaminidase | GalNAc |
| Esophagus | Sialic acid | Hexosaminidase | Sialidase | Sialic acid |
| Esophagus | Galactose | galactosidase | | Galactose |
| Esophagus | Galactose | sialidase | galactosidase | Galactose |
| Esophagus | Fucose | fucosidase | | Fucose |
| Esophagus | Galactose | Galactosidase | | Galactose |
| Esophagus | GlcNAc | hexosaminidase | | GlcNAc |
| Esophagus | Sulfate | Sulfatase | | Sulfate |
| Esophagus | Sulfated hexose | Sulfatase | hexosaminidase | GlcNAc or GalNAc |
| Esophagus | Sulfated uronic acid | Sulfatase | Iduronidase or glucouronidase | IdoA or GlcA |
| Brain | Sialic Acid | Sialidase | | Sialic acid |
| Brain | Sialic Acid | Alpha 2,8 Sialidase | | Sialic acid |
| Brain | Sialic Acid | Alpha 2,3 Sialidase | | Sialic acid |
| Brain | Sialic Acid | Alpha 2,6 Sialidase | | Sialic acid |
| Brain | GalNAc | Hexosaminidase | | GalNAc |
| Brain | GalNAc | Sialidase | Hexosaminidase | GalNAc |
| Brain | Sialic acid | Hexosaminidase | Sialidase | Sialic acid |
| Brain | Galactose | galactosidase | | Galactose |
| Brain | Galactose | sialidase | galactosidase | Galactose |
| Brain | Fucose | fucosidase | | Fucose |
| Brain | Galactose | Galactosidase | | Galactose |
| Brain | GlcNAc | hexosaminidase | | GlcNAc |
| Brain | Sulfate | Sulfatase | | Sulfate |
| Brain | Sulfated hexose | Sulfatase | hexosaminidase | GlcNAc or GalNAc |
| Brain | Sulfated uronic acid | Sulfatase | Iduronidase or glucouronidase | IdoA or GlcA |
| Lymphomas | Sialic Acid | Sialidase | | Sialic acid |
| Lymphomas | Sialic Acid | Alpha 2,8 Sialidase | | Sialic acid |
| Lymphomas | Sialic Acid | Alpha 2,3 Sialidase | | Sialic acid |
| Lymphomas | Sialic Acid | Alpha 2,6 Sialidase | | Sialic acid |
| Lymphomas | GalNAc | Hexosaminidase | | GalNAc |
| Lymphomas | GalNAc | Sialidase | Hexosaminidase | GalNAc |
| Lymphomas | Sialic acid | Hexosaminidase | Sialidase | Sialic acid |
| Lymphomas | Galactose | galactosidase | | Galactose |
| Lymphomas | Galactose | sialidase | galactosidase | Galactose |
| Lymphomas | Fucose | fucosidase | | Fucose |
| Lymphomas | Galactose | Galactosidase | | Galactose |
| Lymphomas | GlcNAc | hexosaminidase | | GlcNAc |
| Lymphomas | Sulfate | Sulfatase | | Sulfate |
| Lymphomas | Sulfated hexose | Sulfatase | hexosaminidase | GlcNAc or GalNAc |
| Lymphomas | Sulfated uronic acid | Sulfatase | Iduronidase or glucouronidase | IdoA or GlcA |
| Leukemias | Sialic Acid | Sialidase | | Sialic acid |
| Leukemias | Sialic Acid | Alpha 2,8 Sialidase | | Sialic acid |
| Leukemias | Sialic Acid | Alpha 2,3 Sialidase | | Sialic acid |
| Leukemias | Sialic Acid | Alpha 2,6 Sialidase | | Sialic acid |
| Leukemias | GalNAc | Hexosaminidase | | GalNAc |
| Leukemias | GalNAc | Sialidase | Hexosaminidase | GalNAc |
| Leukemias | Sialic acid | Hexosaminidase | Sialidase | Sialic acid |
| Leukemias | Galactose | galactosidase | | Galactose |
| Leukemias | Galactose | sialidase | galactosidase | Galactose |
| Leukemias | Fucose | fucosidase | | Fucose |
| Leukemias | Galactose | Galactosidase | | Galactose |

TABLE 2-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Leukemias | GlcNAc | hexosaminidase | | GlcNAc |
| Leukemias | Sulfate | Sulfatase | | Sulfate |
| Leukemias | Sulfated hexose | Sulfatase | hexosaminidase | GlcNAc or GalNAc |
| Leukemias | Sulfated uronic acid | Sulfatase | Iduronidase or glucouronidase | IdoA or GlcA |

Provided herein are methods of diagnosing individuals (including, e.g., a disease state or the severity of a disease states) with a disease state associated with abnormal glycan accumulation. Provided in Table 3 are specific embodiments of disease that are optionally diagnosed and/or monitored according to various embodiments described herein. Table 3 also illustrates various non-limiting embodiments of specific enzyme(s) that are optionally utilized to treat a biological sample from an individual suffering from or suspected of (e.g., through a pre- or preliminary screening process) suffering from various disease states associated with abnormal glycan accumulation. Moreover, Table 3 further illustrates various glycan residual compounds that are liberated in various embodiments described herein, such liberated glycan residual compounds optionally being detected and/or measured in order to diagnose and/or monitor various disease states.

TABLE 3

| Disease | Non-Reducing End Structure | Primary Liberating Enzyme | Secondary Liberating Enzyme | Glycan Residual Compound |
|---|---|---|---|---|
| Alzheimers | Sialic Acid | Sialidase | | Sialic acid |
| Alzheimers | Sialic Acid | Alpha 2,8 Sialidase | | Sialic acid |
| Alzheimers | Sialic Acid | Alpha 2,3 Sialidase | | Sialic acid |
| Alzheimers | Sialic Acid | Alpha 2,6 Sialidase | | Sialic acid |
| Alzheimers | GalNAc | Hexosaminidase | | GalNAc |
| Alzheimers | GalNAc | Sialidase | Hexosaminidase | GalNAc |
| Alzheimers | Sialic acid | Hexosaminidase | Sialidase | Sialic acid |
| Alzheimers | Galactose | galactosidase | | Galactose |
| Alzheimers | Galactose | sialidase | galactosidase | Galactose |
| Alzheimers | Fucose | fucosidase | | Fucose |
| Alzheimers | Galactose | Galactosidase | | Galactose |
| Alzheimers | GlcNAc | hexosaminidase | | GlcNAc |
| Alzheimers | Sulfate | Sulfatase | | Sulfate |
| Alzheimers | Sulfated hexose | Sulfatase | hexosaminidase | GlcNAc or GalNAc |
| Alzheimers | Sulfated uronic acid | Sulfatase | Iduronidase or glucuronidase | IdoA or GlcA |
| Amyotrophic Lateral Sclerosis | Sialic Acid | Sialidase | | Sialic acid |
| Amyotrophic Lateral Sclerosis | Sialic Acid | Alpha 2,8 Sialidase | | Sialic acid |
| Amyotrophic Lateral Sclerosis | Sialic Acid | Alpha 2,3 Sialidase | | Sialic acid |
| Amyotrophic Lateral Sclerosis | Sialic Acid | Alpha 2,6 Sialidase | | Sialic acid |
| Amyotrophic Lateral Sclerosis | GalNAc | Hexosaminidase | | GalNAc |
| Amyotrophic Lateral Sclerosis | GalNAc | Sialidase | Hexosaminidase | GalNAc |
| Amyotrophic Lateral Sclerosis | Sialic acid | Hexosaminidase | Sialidase | Sialic acid |
| Amyotrophic Lateral Sclerosis | Galactose | galactosidase | | Galactose |
| Amyotrophic Lateral Sclerosis | Galactose | sialidase | galactosidase | Galactose |
| Amyotrophic Lateral Sclerosis | Fucose | fucosidase | | Fucose |
| Amyotrophic Lateral Sclerosis | Galactose | Galactosidase | | Galactose |
| Amyotrophic Lateral Sclerosis | GlcNAc | hexosaminidase | | GlcNAc |

TABLE 3-continued

| Disease | Non-Reducing End Structure | Primary Liberating Enzyme | Secondary Liberating Enzyme | Glycan Residual Compound |
|---|---|---|---|---|
| Amyotrophic Lateral Sclerosis | Sulfate | Sulfatase | | Sulfate |
| Amyotrophic Lateral Sclerosis | Sulfated hexose | Sulfatase | hexosaminidase | GlcNAc or GalNAc |
| Amyotrophic Lateral Sclerosis | Sulfated uronic acid | Sulfatase | Iduronidase or glucuronidase | IdoA or GlcA |
| Cerebral Palsy | Sialic Acid | Sialidase | | Sialic acid |
| Cerebral Palsy | Sialic Acid | Alpha 2,8 Sialidase | | Sialic acid |
| Cerebral Palsy | Sialic Acid | Alpha 2,3 Sialidase | | Sialic acid |
| Cerebral Palsy | Sialic Acid | Alpha 2,6 Sialidase | | Sialic acid |
| Cerebral Palsy | GalNAc | Hexosaminidase | | GalNAc |
| Cerebral Palsy | GalNAc | Sialidase | Hexosaminidase | GalNAc |
| Cerebral Palsy | Sialic acid | Hexosaminidase | Sialidase | Sialic acid |
| Cerebral Palsy | Galactose | galactosidase | | Galactose |
| Cerebral Palsy | Galactose | sialidase | galactosidase | Galactose |
| Cerebral Palsy | Fucose | fucosidase | | Fucose |
| Cerebral Palsy | Galactose | Galactosidase | | Galactose |
| Cerebral Palsy | GlcNAc | hexosaminidase | | GlcNAc |
| Cerebral Palsy | Sulfate | Sulfatase | | Sulfate |
| Cerebral Palsy | Sulfated hexose | Sulfatase | hexosaminidase | GlcNAc or GalNAc |
| Cerebral Palsy | Sulfated uronic acid | Sulfatase | Iduronidase or glucuronidase | IdoA or GlcA |
| Schizophrenia | Sialic Acid | Sialidase | | Sialic acid |
| Schizophrenia | Sialic Acid | Alpha 2,8 Sialidase | | Sialic acid |
| Schizophrenia | Sialic Acid | Alpha 2,3 Sialidase | | Sialic acid |
| Schizophrenia | Sialic Acid | Alpha 2,6 Sialidase | | Sialic acid |
| Schizophrenia | GalNAc | Hexosaminidase | | GalNAc |
| Schizophrenia | GalNAc | Sialidase | Hexosaminidase | GalNAc |
| Schizophrenia | Sialic acid | Hexosaminidase | Sialidase | Sialic acid |
| Schizophrenia | Galactose | galactosidase | | Galactose |
| Schizophrenia | Galactose | sialidase | galactosidase | Galactose |
| Schizophrenia | Fucose | fucosidase | | Fucose |
| Schizophrenia | Galactose | Galactosidase | | Galactose |
| Schizophrenia | GlcNAc | hexosaminidase | | GlcNAc |
| Schizophrenia | Sulfate | Sulfatase | | Sulfate |
| Schizophrenia | Sulfated hexose | Sulfatase | hexosaminidase | GlcNAc or GalNAc |
| Schizophrenia | Sulfated uronic acid | Sulfatase | Iduronidase or glucouronidase | IdoA or GlcA |
| Bipolar Disorder | Sialic Acid | Sialidase | | Sialic acid |
| Bipolar Disorder | Sialic Acid | Alpha 2,8 Sialidase | | Sialic acid |
| Bipolar Disorder | Sialic Acid | Alpha 2,3 Sialidase | | Sialic acid |
| Bipolar Disorder | Sialic Acid | Alpha 2,6 Sialidase | | Sialic acid |
| Bipolar Disorder | GalNAc | Hexosaminidase | | GalNAc |
| Bipolar Disorder | GalNAc | Sialidase | Hexosaminidase | GalNAc |
| Bipolar Disorder | Sialic acid | Hexosaminidase | Sialidase | Sialic acid |
| Bipolar Disorder | Galactose | galactosidase | | Galactose |
| Bipolar Disorder | Galactose | sialidase | galactosidase | Galactose |
| Bipolar Disorder | Fucose | fucosidase | | Fucose |
| Bipolar Disorder | Galactose | Galactosidase | | Galactose |
| Bipolar Disorder | GlcNAc | hexosaminidase | | GlcNAc |
| Bipolar Disorder | Sulfate | Sulfatase | | Sulfate |
| Bipolar Disorder | Sulfated hexose | Sulfatase | hexosaminidase | GlcNAc or GalNAc |
| Bipolar Disorder | Sulfated uronic acid | Sulfatase | Iduronidase or glucouronidase | IdoA or GlcA |
| Depression | Sialic Acid | Sialidase | | Sialic acid |
| Depression | Sialic Acid | Alpha 2,8 Sialidase | | Sialic acid |
| Depression | Sialic Acid | Alpha 2,3 Sialidase | | Sialic acid |
| Depression | Sialic Acid | Alpha 2,6 Sialidase | | Sialic acid |
| Depression | GalNAc | Hexosaminidase | | GalNAc |
| Depression | GalNAc | Sialidase | Hexosaminidase | GalNAc |

TABLE 3-continued

| Disease | Non-Reducing End Structure | Primary Liberating Enzyme | Secondary Liberating Enzyme | Glycan Residual Compound |
|---|---|---|---|---|
| Depression | Sialic acid | Hexosaminidase | Sialidase | Sialic acid |
| Depression | Galactose | galactosidase | | Galactose |
| Depression | Galactose | sialidase | galactosidase | Galactose |
| Depression | Fucose | fucosidase | | Fucose |
| Depression | Galactose | Galactosidase | | Galactose |
| Depression | GlcNAc | hexosaminidase | | GlcNAc |
| Depression | Sulfate | Sulfatase | | Sulfate |
| Depression | Sulfated hexose | Sulfatase | hexosaminidase | GlcNAc or GalNAc |
| Depression | Sulfated uronic acid | Sulfatase | Iduronidase or glucouronidase | IdoA or GlcA |
| Epilepsy | Sialic Acid | Sialidase | | Sialic acid |
| Epilepsy | Sialic Acid | Alpha 2,8 Sialidase | | Sialic acid |
| Epilepsy | Sialic Acid | Alpha 2,3 Sialidase | | Sialic acid |
| Epilepsy | Sialic Acid | Alpha 2,6 Sialidase | | Sialic acid |
| Epilepsy | GalNAc | Hexosaminidase | | GalNAc |
| Epilepsy | GalNAc | Sialidase | Hexosaminidase | GalNAc |
| Epilepsy | Sialic acid | Hexosaminidase | Sialidase | Sialic acid |
| Epilepsy | Galactose | galactosidase | | Galactose |
| Epilepsy | Galactose | sialidase | galactosidase | Galactose |
| Epilepsy | Fucose | fucosidase | | Fucose |
| Epilepsy | Galactose | Galactosidase | | Galactose |
| Epilepsy | GlcNAc | hexosaminidase | | GlcNAc |
| Epilepsy | Sulfate | Sulfatase | | Sulfate |
| Epilepsy | Sulfated hexose | Sulfatase | hexosaminidase | GlcNAc or GalNAc |
| Epilepsy | Sulfated uronic acid | Sulfatase | Iduronidase or glucouronidase | IdoA or GlcA |
| Migraine | Sialic Acid | Sialidase | | Sialic acid |
| Migraine | Sialic Acid | Alpha 2,8 Sialidase | | Sialic acid |
| Migraine | Sialic Acid | Alpha 2,3 Sialidase | | Sialic acid |
| Migraine | Sialic Acid | Alpha 2,6 Sialidase | | Sialic acid |
| Migraine | GalNAc | Hexosaminidase | | GalNAc |
| Migraine | GalNAc | Sialidase | Hexosaminidase | GalNAc |
| Migraine | Sialic acid | Hexosaminidase | Sialidase | Sialic acid |
| Migraine | Galactose | galactosidase | | Galactose |
| Migraine | Galactose | sialidase | galactosidase | Galactose |
| Migraine | Fucose | fucosidase | | Fucose |
| Migraine | Galactose | Galactosidase | | Galactose |
| Migraine | GlcNAc | hexosaminidase | | GlcNAc |
| Migraine | Sulfate | Sulfatase | | Sulfate |
| Migraine | Sulfated hexose | Sulfatase | hexosaminidase | GlcNAc or GalNAc |
| Migraine | Sulfated uronic acid | Sulfatase | Iduronidase or glucouronidase | IdoA or GlcA |
| Multiple Sclerosis | Sialic Acid | Sialidase | | Sialic acid |
| Multiple Sclerosis | Sialic Acid | Alpha 2,8 Sialidase | | Sialic acid |
| Multiple Sclerosis | Sialic Acid | Alpha 2,3 Sialidase | | Sialic acid |
| Multiple Sclerosis | Sialic Acid | Alpha 2,6 Sialidase | | Sialic acid |
| Multiple Sclerosis | GalNAc | Hexosaminidase | | GalNAc |
| Multiple Sclerosis | GalNAc | Sialidase | Hexosaminidase | GalNAc |
| Multiple Sclerosis | Sialic acid | Hexosaminidase | Sialidase | Sialic acid |
| Multiple Sclerosis | Galactose | galactosidase | | Galactose |
| Multiple Sclerosis | Galactose | sialidase | galactosidase | Galactose |
| Multiple Sclerosis | Fucose | fucosidase | | Fucose |
| Multiple Sclerosis | Galactose | Galactosidase | | Galactose |
| Multiple Sclerosis | GlcNAc | hexosaminidase | | GlcNAc |
| Multiple Sclerosis | Sulfate | Sulfatase | | Sulfate |
| Multiple Sclerosis | Sulfated hexose | Sulfatase | hexosaminidase | GlcNAc or GalNAc |
| Multiple Sclerosis | Sulfated uronic acid | Sulfatase | Iduronidase or glucouronidase | IdoA or GlcA |
| Parkinson's | Sialic Acid | Sialidase | | Sialic acid |
| Parkinson's | Sialic Acid | Alpha 2,8 Sialidase | | Sialic acid |

TABLE 3-continued

| Disease | Non-Reducing End Structure | Primary Liberating Enzyme | Secondary Liberating Enzyme | Glycan Residual Compound |
|---|---|---|---|---|
| Parkinson's | Sialic Acid | Alpha 2,3 Sialidase | | Sialic acid |
| Parkinson's | Sialic Acid | Alpha 2,6 Sialidase | | Sialic acid |
| Parkinson's | GalNAc | Hexosaminidase | | GalNAc |
| Parkinson's | GalNAc | Sialidase | Hexosaminidase | GalNAc |
| Parkinson's | Sialic acid | Hexosaminidase | Sialidase | Sialic acid |
| Parkinson's | Galactose | galactosidase | | Galactose |
| Parkinson's | Galactose | sialidase | galactosidase | Galactose |
| Parkinson's | Fucose | fucosidase | | Fucose |
| Parkinson's | Galactose | Galactosidase | | Galactose |
| Parkinson's | GlcNAc | hexosaminidase | | GlcNAc |
| Parkinson's | Sulfate | Sulfatase | | Sulfate |
| Parkinson's | Sulfated hexose | Sulfatase | hexosaminidase | GlcNAc or GalNAc |
| Parkinson's | Sulfated uronic acid | Sulfatase | Iduronidase or glucouronidase | IdoA or GlcA |
| Rheumatoid Arthritis | Sialic Acid | Sialidase | | Sialic acid |
| Rheumatoid Arthritis | Sialic Acid | Alpha 2,8 Sialidase | | Sialic acid |
| Rheumatoid Arthritis | Sialic Acid | Alpha 2,3 Sialidase | | Sialic acid |
| Rheumatoid Arthritis | Sialic Acid | Alpha 2,6 Sialidase | | Sialic acid |
| Rheumatoid Arthritis | GalNAc | Hexosaminidase | | GalNAc |
| Rheumatoid Arthritis | GalNAc | Sialidase | Hexosaminidase | GalNAc |
| Rheumatoid Arthritis | Sialic acid | Hexosaminidase | Sialidase | Sialic acid |
| Rheumatoid Arthritis | Galactose | galactosidase | | Galactose |
| Rheumatoid Arthritis | Galactose | sialidase | galactosidase | Galactose |
| Rheumatoid Arthritis | Fucose | fucosidase | | Fucose |
| Rheumatoid Arthritis | Galactose | Galactosidase | | Galactose |
| Rheumatoid Arthritis | GlcNAc | hexosaminidase | | GlcNAc |
| Rheumatoid Arthritis | Sulfate | Sulfatase | | Sulfate |
| Rheumatoid Arthritis | Sulfated hexose | Sulfatase | hexosaminidase | GlcNAc or GalNAc |
| Rheumatoid Arthritis | Sulfated uronic acid | Sulfatase | Iduronidase or glucouronidase | IdoA or GlcA |
| Psoriatic Arthritis | Sialic Acid | Sialidase | | Sialic acid |
| Psoriatic Arthritis | Sialic Acid | Alpha 2,8 Sialidase | | Sialic acid |
| Psoriatic Arthritis | Sialic Acid | Alpha 2,3 Sialidase | | Sialic acid |
| Psoriatic Arthritis | Sialic Acid | Alpha 2,6 Sialidase | | Sialic acid |
| Psoriatic Arthritis | GalNAc | Hexosaminidase | | GalNAc |
| Psoriatic Arthritis | GalNAc | Sialidase | Hexosaminidase | GalNAc |
| Psoriatic Arthritis | Sialic acid | Hexosaminidase | Sialidase | Sialic acid |
| Psoriatic Arthritis | Galactose | galactosidase | | Galactose |
| Psoriatic Arthritis | Galactose | sialidase | galactosidase | Galactose |
| Psoriatic Arthritis | Fucose | fucosidase | | Fucose |
| Psoriatic Arthritis | Galactose | Galactosidase | | Galactose |
| Psoriatic Arthritis | GlcNAc | hexosaminidase | | GlcNAc |
| Psoriatic Arthritis | Sulfate | Sulfatase | | Sulfate |
| Psoriatic Arthritis | Sulfated hexose | Sulfatase | hexosaminidase | GlcNAc or GalNAc |
| Psoriatic Arthritis | Sulfated uronic acid | Sulfatase | Iduronidase or glucouronidase | IdoA or GlcA |
| Asthma | Sialic Acid | Sialidase | | Sialic acid |
| Asthma | Sialic Acid | Alpha 2,8 Sialidase | | Sialic acid |
| Asthma | Sialic Acid | Alpha 2,3 Sialidase | | Sialic acid |
| Asthma | Sialic Acid | Alpha 2,6 Sialidase | | Sialic acid |
| Asthma | GalNAc | Hexosaminidase | | GalNAc |
| Asthma | GalNAc | Sialidase | Hexosaminidase | GalNAc |
| Asthma | Sialic acid | Hexosaminidase | Sialidase | Sialic acid |
| Asthma | Galactose | galactosidase | | Galactose |
| Asthma | Galactose | sialidase | galactosidase | Galactose |
| Asthma | Fucose | fucosidase | | Fucose |
| Asthma | Galactose | Galactosidase | | Galactose |
| Asthma | GlcNAc | hexosaminidase | | GlcNAc |
| Asthma | Sulfate | Sulfatase | | Sulfate |
| Asthma | Sulfated hexose | Sulfatase | hexosaminidase | GlcNAc or GalNAc |

TABLE 3-continued

| Disease | Non-Reducing End Structure | Primary Liberating Enzyme | Secondary Liberating Enzyme | Glycan Residual Compound |
|---|---|---|---|---|
| Asthma | Sulfated uronic acid | Sulfatase | Iduronidase or glucouronidase | IdoA or GlcA |
| Chronic Obstructive Pulmonary Disorder | Sialic Acid | Sialidase | | Sialic acid |
| Chronic Obstructive Pulmonary Disorder | Sialic Acid | Alpha 2,8 Sialidase | | Sialic acid |
| Chronic Obstructive Pulmonary Disorder | Sialic Acid | Alpha 2,3 Sialidase | | Sialic acid |
| Chronic Obstructive Pulmonary Disorder | Sialic Acid | Alpha 2,6 Sialidase | | Sialic acid |
| Chronic Obstructive Pulmonary Disorder | GalNAc | Hexosaminidase | | GalNAc |
| Chronic Obstructive Pulmonary Disorder | GalNAc | Sialidase | Hexosaminidase | GalNAc |
| Chronic Obstructive Pulmonary Disorder | Sialic acid | Hexosaminidase | Sialidase | Sialic acid |
| Chronic Obstructive Pulmonary Disorder | Galactose | galactosidase | | Galactose |
| Chronic Obstructive Pulmonary Disorder | Galactose | sialidase | galactosidase | Galactose |
| Chronic Obstructive Pulmonary Disorder | Fucose | fucosidase | | Fucose |
| Chronic Obstructive Pulmonary Disorder | Galactose | Galactosidase | | Galactose |
| Chronic Obstructive Pulmonary Disorder | GlcNAc | hexosaminidase | | GlcNAc |
| Chronic Obstructive Pulmonary Disorder | Sulfate | Sulfatase | | Sulfate |
| Chronic Obstructive Pulmonary Disorder | Sulfated hexose | Sulfatase | hexosaminidase | GlcNAc or GalNAc |
| Chronic Obstructive Pulmonary Disorder | Sulfated uronic acid | Sulfatase | Iduronidase or glucouronidase | IdoA or GlcA |
| Lupus | Sialic Acid | Sialidase | | Sialic acid |
| Lupus | Sialic Acid | Alpha 2,8 Sialidase | | Sialic acid |
| Lupus | Sialic Acid | Alpha 2,3 Sialidase | | Sialic acid |
| Lupus | Sialic Acid | Alpha 2,6 Sialidase | | Sialic acid |
| Lupus | GalNAc | Hexosaminidase | | GalNAc |
| Lupus | GalNAc | Sialidase | Hexosaminidase | GalNAc |
| Lupus | Sialic acid | Hexosaminidase | Sialidase | Sialic acid |
| Lupus | Galactose | galactosidase | | Galactose |
| Lupus | Galactose | sialidase | galactosidase | Galactose |
| Lupus | Fucose | fucosidase | | Fucose |
| Lupus | Galactose | Galactosidase | | Galactose |
| Lupus | GlcNAc | hexosaminidase | | GlcNAc |
| Lupus | Sulfate | Sulfatase | | Sulfate |
| Lupus | Sulfated hexose | Sulfatase | hexosaminidase | GlcNAc or GalNAc |
| Lupus | Sulfated uronic acid | Sulfatase | Iduronidase or glucouronidase | IdoA or GlcA |
| Hepatitis | Sialic Acid | Sialidase | | Sialic acid |
| Hepatitis | Sialic Acid | Alpha 2,8 Sialidase | | Sialic acid |
| Hepatitis | Sialic Acid | Alpha 2,3 Sialidase | | Sialic acid |
| Hepatitis | Sialic Acid | Alpha 2,6 Sialidase | | Sialic acid |
| Hepatitis | GalNAc | Hexosaminidase | | GalNAc |
| Hepatitis | GalNAc | Sialidase | Hexosaminidase | GalNAc |
| Hepatitis | Sialic acid | Hexosaminidase | Sialidase | Sialic acid |
| Hepatitis | Galactose | galactosidase | | Galactose |
| Hepatitis | Galactose | sialidase | galactosidase | Galactose |
| Hepatitis | Fucose | fucosidase | | Fucose |
| Hepatitis | Galactose | Galactosidase | | Galactose |
| Hepatitis | GlcNAc | hexosaminidase | | GlcNAc |
| Hepatitis | Sulfate | Sulfatase | | Sulfate |
| Hepatitis | Sulfated hexose | Sulfatase | hexosaminidase | GlcNAc or GalNAc |
| Hepatitis | Sulfated uronic acid | Sulfatase | Iduronidase or glucouronidase | IdoA or GlcA |
| Renal Disease | Sialic Acid | Sialidase | | Sialic acid |
| Renal Disease | Sialic Acid | Alpha 2,8 Sialidase | | Sialic acid |

TABLE 3-continued

| Disease | Non-Reducing End Structure | Primary Liberating Enzyme | Secondary Liberating Enzyme | Glycan Residual Compound |
|---|---|---|---|---|
| Renal Disease | Sialic Acid | Alpha 2,3 Sialidase | | Sialic acid |
| Renal Disease | Sialic Acid | Alpha 2,6 Sialidase | | Sialic acid |
| Renal Disease | GalNAc | Hexosaminidase | | GalNAc |
| Renal Disease | GalNAc | Sialidase | Hexosaminidase | GalNAc |
| Renal Disease | Sialic acid | Hexosaminidase | Sialidase | Sialic acid |
| Renal Disease | Galactose | galactosidase | | Galactose |
| Renal Disease | Galactose | sialidase | galactosidase | Galactose |
| Renal Disease | Fucose | fucosidase | | Fucose |
| Renal Disease | Galactose | Galactosidase | | Galactose |
| Renal Disease | GlcNAc | hexosaminidase | | GlcNAc |
| Renal Disease | Sulfate | Sulfatase | | Sulfate |
| Renal Disease | Sulfated hexose | Sulfatase | hexosaminidase | GlcNAc or GalNAc |
| Renal Disease | Sulfated uronic acid | Sulfatase | Iduronidase or glucouronidase | IdoA or GlcA |
| Sickle Cell Disease | Sialic Acid | Sialidase | | Sialic acid |
| Sickle Cell Disease | Sialic Acid | Alpha 2,8 Sialidase | | Sialic acid |
| Sickle Cell Disease | Sialic Acid | Alpha 2,3 Sialidase | | Sialic acid |
| Sickle Cell Disease | Sialic Acid | Alpha 2,6 Sialidase | | Sialic acid |
| Sickle Cell Disease | GalNAc | Hexosaminidase | | GalNAc |
| Sickle Cell Disease | GalNAc | Sialidase | Hexosaminidase | GalNAc |
| Sickle Cell Disease | Sialic acid | Hexosaminidase | Sialidase | Sialic acid |
| Sickle Cell Disease | Galactose | galactosidase | | Galactose |
| Sickle Cell Disease | Galactose | sialidase | galactosidase | Galactose |
| Sickle Cell Disease | Fucose | fucosidase | | Fucose |
| Sickle Cell Disease | Galactose | Galactosidase | | Galactose |
| Sickle Cell Disease | GlcNAc | hexosaminidase | | GlcNAc |
| Sickle Cell Disease | Sulfate | Sulfatase | | Sulfate |
| Sickle Cell Disease | Sulfated hexose | Sulfatase | hexosaminidase | GlcNAc or GalNAc |
| Sickle Cell Disease | Sulfated uronic acid | Sulfatase | Iduronidase or glucouronidase | IdoA or GlcA |
| Fibromyalgia | Sialic Acid | Sialidase | | Sialic acid |
| Fibromyalgia | Sialic Acid | Alpha 2,8 Sialidase | | Sialic acid |
| Fibromyalgia | Sialic Acid | Alpha 2,3 Sialidase | | Sialic acid |
| Fibromyalgia | Sialic Acid | Alpha 2,6 Sialidase | | Sialic acid |
| Fibromyalgia | GalNAc | Hexosaminidase | | GalNAc |
| Fibromyalgia | GalNAc | Sialidase | Hexosaminidase | GalNAc |
| Fibromyalgia | Sialic acid | Hexosaminidase | Sialidase | Sialic acid |
| Fibromyalgia | Galactose | galactosidase | | Galactose |
| Fibromyalgia | Galactose | sialidase | galactosidase | Galactose |
| Fibromyalgia | Fucose | fucosidase | | Fucose |
| Fibromyalgia | Galactose | Galactosidase | | Galactose |
| Fibromyalgia | GlcNAc | hexosaminidase | | GlcNAc |
| Fibromyalgia | Sulfate | Sulfatase | | Sulfate |
| Fibromyalgia | Sulfated hexose | Sulfatase | hexosaminidase | GlcNAc or GalNAc |
| Fibromyalgia | Sulfated uronic acid | Sulfatase | Iduronidase or glucouronidase | IdoA or GlcA |
| Irritable Bowel Syndrome | Sialic Acid | Sialidase | | Sialic acid |
| Irritable Bowel Syndrome | Sialic Acid | Alpha 2,8 Sialidase | | Sialic acid |
| Irritable Bowel Syndrome | Sialic Acid | Alpha 2,3 Sialidase | | Sialic acid |
| Irritable Bowel Syndrome | Sialic Acid | Alpha 2,6 Sialidase | | Sialic acid |
| Irritable Bowel Syndrome | GalNAc | Hexosaminidase | | GalNAc |
| Irritable Bowel Syndrome | GalNAc | Sialidase | Hexosaminidase | GalNAc |
| Irritable Bowel Syndrome | Sialic acid | Hexosaminidase | Sialidase | Sialic acid |
| Irritable Bowel Syndrome | Galactose | galactosidase | | Galactose |
| Irritable Bowel Syndrome | Galactose | sialidase | galactosidase | Galactose |

TABLE 3-continued

| Disease | Non-Reducing End Structure | Primary Liberating Enzyme | Secondary Liberating Enzyme | Glycan Residual Compound |
|---|---|---|---|---|
| Irritable Bowel Syndrome | Fucose | fucosidase | | Fucose |
| Irritable Bowel Syndrome | Galactose | Galactosidase | | Galactose |
| Irritable Bowel Syndrome | GlcNAc | hexosaminidase | | GlcNAc |
| Irritable Bowel Syndrome | Sulfate | Sulfatase | | Sulfate |
| Irritable Bowel Syndrome | Sulfated hexose | Sulfatase | hexosaminidase | GlcNAc or GalNAc |
| Irritable Bowel Syndrome | Sulfated uronic acid | Sulfatase | Iduronidase or glucouronidase | IdoA or GlcA |
| Ulcer | Sialic Acid | Sialidase | | Sialic acid |
| Ulcer | Sialic Acid | Alpha 2,8 Sialidase | | Sialic acid |
| Ulcer | Sialic Acid | Alpha 2,3 Sialidase | | Sialic acid |
| Ulcer | Sialic Acid | Alpha 2,6 Sialidase | | Sialic acid |
| Ulcer | GalNAc | Hexosaminidase | | GalNAc |
| Ulcer | GalNAc | Sialidase | Hexosaminidase | GalNAc |
| Ulcer | Sialic acid | Hexosaminidase | Sialidase | Sialic acid |
| Ulcer | Galactose | galactosidase | | Galactose |
| Ulcer | Galactose | sialidase | galactosidase | Galactose |
| Ulcer | Fucose | fucosidase | | Fucose |
| Ulcer | Galactose | Galactosidase | | Galactose |
| Ulcer | GlcNAc | hexosaminidase | | GlcNAc |
| Ulcer | Sulfate | Sulfatase | | Sulfate |
| Ulcer | Sulfated hexose | Sulfatase | hexosaminidase | GlcNAc or GalNAc |
| Ulcer | Sulfated uronic acid | Sulfatase | Iduronidase or glucouronidase | IdoA or GlcA |
| Irritable Bowel Disease | Sialic Acid | Sialidase | | Sialic acid |
| Irritable Bowel Disease | Sialic Acid | Alpha 2,8 Sialidase | | Sialic acid |
| Irritable Bowel Disease | Sialic Acid | Alpha 2,3 Sialidase | | Sialic acid |
| Irritable Bowel Disease | Sialic Acid | Alpha 2,6 Sialidase | | Sialic acid |
| Irritable Bowel Disease | GalNAc | Hexosaminidase | | GalNAc |
| Irritable Bowel Disease | GalNAc | Sialidase | Hexosaminidase | GalNAc |
| Irritable Bowel Disease | Sialic acid | Hexosaminidase | Sialidase | Sialic acid |
| Irritable Bowel Disease | Galactose | galactosidase | | Galactose |
| Irritable Bowel Disease | Galactose | sialidase | galactosidase | Galactose |
| Irritable Bowel Disease | Fucose | fucosidase | | Fucose |
| Irritable Bowel Disease | Galactose | Galactosidase | | Galactose |
| Irritable Bowel Disease | GlcNAc | hexosaminidase | | GlcNAc |
| Irritable Bowel Disease | Sulfate | Sulfatase | | Sulfate |
| Irritable Bowel Disease | Sulfated hexose | Sulfatase | hexosaminidase | GlcNAc or GalNAc |
| Irritable Bowel Disease | Sulfated uronic acid | Sulfatase | Iduronidase or glucouronidase | IdoA or GlcA |
| Coronary Artery Disease | Sialic Acid | Sialidase | | Sialic acid |
| Coronary Artery Disease | Sialic Acid | Alpha 2,8 Sialidase | | Sialic acid |
| Coronary Artery Disease | Sialic Acid | Alpha 2,3 Sialidase | | Sialic acid |
| Coronary Artery Disease | Sialic Acid | Alpha 2,6 Sialidase | | Sialic acid |
| Coronary Artery Disease | GalNAc | Hexosaminidase | | GalNAc |
| Coronary Artery Disease | GalNAc | Sialidase | Hexosaminidase | GalNAc |
| Coronary Artery Disease | Sialic acid | Hexosaminidase | Sialidase | Sialic acid |
| Coronary Artery Disease | Galactose | galactosidase | | Galactose |
| Coronary Artery Disease | Galactose | sialidase | galactosidase | Galactose |
| Coronary Artery Disease | Fucose | fucosidase | | Fucose |
| Coronary Artery Disease | Galactose | Galactosidase | | Galactose |
| Coronary Artery Disease | GlcNAc | hexosaminidase | | GlcNAc |
| Coronary Artery Disease | Sulfate | Sulfatase | | Sulfate |
| Coronary Artery Disease | Sulfated hexose | Sulfatase | hexosaminidase | GlcNAc or GalNAc |
| Coronary Artery Disease | Sulfated uronic acid | Sulfatase | Iduronidase or glucouronidase | IdoA or GlcA |
| Restenosis | Sialic Acid | Sialidase | | Sialic acid |
| Restenosis | Sialic Acid | Alpha 2,8 Sialidase | | Sialic acid |

TABLE 3-continued

| Disease | Non-Reducing End Structure | Primary Liberating Enzyme | Secondary Liberating Enzyme | Glycan Residual Compound |
|---|---|---|---|---|
| Restenosis | Sialic Acid | Alpha 2,3 Sialidase | | Sialic acid |
| Restenosis | Sialic Acid | Alpha 2,6 Sialidase | | Sialic acid |
| Restenosis | GalNAc | Hexosaminidase | | GalNAc |
| Restenosis | GalNAc | Sialidase | Hexosaminidase | GalNAc |
| Restenosis | Sialic acid | Hexosaminidase | Sialidase | Sialic acid |
| Restenosis | Galactose | galactosidase | | Galactose |
| Restenosis | Galactose | sialidase | galactosidase | Galactose |
| Restenosis | Fucose | fucosidase | | Fucose |
| Restenosis | Galactose | Galactosidase | | Galactose |
| Restenosis | GlcNAc | hexosaminidase | | GlcNAc |
| Restenosis | Sulfate | Sulfatase | | Sulfate |
| Restenosis | Sulfated hexose | Sulfatase | hexosaminidase | GlcNAc or GalNAc |
| Restenosis | Sulfated uronic acid | Sulfatase | Iduronidase or glucouronidase | IdoA or GlcA |
| Stroke | Sialic Acid | Sialidase | | Sialic acid |
| Stroke | Sialic Acid | Alpha 2,8 Sialidase | | Sialic acid |
| Stroke | Sialic Acid | Alpha 2,3 Sialidase | | Sialic acid |
| Stroke | Sialic Acid | Alpha 2,6 Sialidase | | Sialic acid |
| Stroke | GalNAc | Hexosaminidase | | GalNAc |
| Stroke | GalNAc | Sialidase | Hexosaminidase | GalNAc |
| Stroke | Sialic acid | Hexosaminidase | Sialidase | Sialic acid |
| Stroke | Galactose | galactosidase | | Galactose |
| Stroke | Galactose | sialidase | galactosidase | Galactose |
| Stroke | Fucose | fucosidase | | Fucose |
| Stroke | Galactose | Galactosidase | | Galactose |
| Stroke | GlcNAc | hexosaminidase | | GlcNAc |
| Stroke | Sulfate | Sulfatase | | Sulfate |
| Stroke | Sulfated hexose | Sulfatase | hexosaminidase | GlcNAc or GalNAc |
| Stroke | Sulfated uronic acid | Sulfatase | Iduronidase or glucouronidase | IdoA or GlcA |
| Diabetes | Sialic Acid | Sialidase | | Sialic acid |
| Diabetes | Sialic Acid | Alpha 2,8 Sialidase | | Sialic acid |
| Diabetes | Sialic Acid | Alpha 2,3 Sialidase | | Sialic acid |
| Diabetes | Sialic Acid | Alpha 2,6 Sialidase | | Sialic acid |
| Diabetes | GalNAc | Hexosaminidase | | GalNAc |
| Diabetes | GalNAc | Sialidase | Hexosaminidase | GalNAc |
| Diabetes | Sialic acid | Hexosaminidase | Sialidase | Sialic acid |
| Diabetes | Galactose | galactosidase | | Galactose |
| Diabetes | Galactose | sialidase | galactosidase | Galactose |
| Diabetes | Fucose | fucosidase | | Fucose |
| Diabetes | Galactose | Galactosidase | | Galactose |
| Diabetes | GlcNAc | hexosaminidase | | GlcNAc |
| Diabetes | Sulfate | Sulfatase | | Sulfate |
| Diabetes | Sulfated hexose | Sulfatase | hexosaminidase | GlcNAc or GalNAc |
| Diabetes | Sulfated uronic acid | Sulfatase | Iduronidase or glucouronidase | IdoA or GlcA |
| Hyperheparanemia | Sialic Acid | Sialidase | | Sialic acid |
| Hyperheparanemia | Sialic Acid | Alpha 2,8 Sialidase | | Sialic acid |
| Hyperheparanemia | Sialic Acid | Alpha 2,3 Sialidase | | Sialic acid |
| Hyperheparanemia | Sialic Acid | Alpha 2,6 Sialidase | | Sialic acid |
| Hyperheparanemia | GalNAc | Hexosaminidase | | GalNAc |
| Hyperheparanemia | GalNAc | Sialidase | Hexosaminidase | GalNAc |
| Hyperheparanemia | Sialic acid | Hexosaminidase | Sialidase | Sialic acid |
| Hyperheparanemia | Galactose | galactosidase | | Galactose |
| Hyperheparanemia | Galactose | sialidase | galactosidase | Galactose |
| Hyperheparanemia | Fucose | fucosidase | | Fucose |
| Hyperheparanemia | Galactose | Galactosidase | | Galactose |
| Hyperheparanemia | GlcNAc | hexosaminidase | | GlcNAc |
| Hyperheparanemia | Sulfate | Sulfatase | | Sulfate |
| Hyperheparanemia | Sulfated hexose | Sulfatase | hexosaminidase | GlcNAc or GalNAc |

TABLE 3-continued

| Disease | Non-Reducing End Structure | Primary Liberating Enzyme | Secondary Liberating Enzyme | Glycan Residual Compound |
|---|---|---|---|---|
| Hyperheparanemia | Sulfated uronic acid | Sulfatase | Iduronidase or glucouronidase | IdoA or GlcA |
| Hypergangliosidemia | Sialic Acid | Sialidase | | Sialic acid |
| Hypergangliosidemia | Sialic Acid | Alpha 2,8 Sialidase | | Sialic acid |
| Hypergangliosidemia | Sialic Acid | Alpha 2,3 Sialidase | | Sialic acid |
| Hypergangliosidemia | Sialic Acid | Alpha 2,6 Sialidase | | Sialic acid |
| Hypergangliosidemia | GalNAc | Hexosaminidase | | GalNAc |
| Hypergangliosidemia | GalNAc | Sialidase | Hexosaminidase | GalNAc |
| Hypergangliosidemia | Sialic acid | Hexosaminidase | Sialidase | Sialic acid |
| Hypergangliosidemia | Galactose | galactosidase | | Galactose |
| Hypergangliosidemia | Galactose | sialidase | galactosidase | Galactose |
| Hypergangliosidemia | Fucose | fucosidase | | Fucose |
| Hypergangliosidemia | Galactose | Galactosidase | | Galactose |
| Hypergangliosidemia | GlcNAc | hexosaminidase | | GlcNAc |
| Hypergangliosidemia | Sulfate | Sulfatase | | Sulfate |
| Hypergangliosidemia | Sulfated hexose | Sulfatase | hexosaminidase | GlcNAc or GalNAc |
| Hypergangliosidemia | Sulfated uronic acid | Sulfatase | Iduronidase or glucouronidase | IdoA or GlcA |
| Hypermucinemia | Sialic Acid | Sialidase | | Sialic acid |
| Hypermucinemia | Sialic Acid | Alpha 2,8 Sialidase | | Sialic acid |
| Hypermucinemia | Sialic Acid | Alpha 2,3 Sialidase | | Sialic acid |
| Hypermucinemia | Sialic Acid | Alpha 2,6 Sialidase | | Sialic acid |
| Hypermucinemia | GalNAc | Hexosaminidase | | GalNAc |
| Hypermucinemia | GalNAc | Sialidase | Hexosaminidase | GalNAc |
| Hypermucinemia | Sialic acid | Hexosaminidase | Sialidase | Sialic acid |
| Hypermucinemia | Galactose | galactosidase | | Galactose |
| Hypermucinemia | Galactose | sialidase | galactosidase | Galactose |
| Hypermucinemia | Fucose | fucosidase | | Fucose |
| Hypermucinemia | Galactose | Galactosidase | | Galactose |
| Hypermucinemia | GlcNAc | hexosaminidase | | GlcNAc |
| Hypermucinemia | Sulfate | Sulfatase | | Sulfate |
| Hypermucinemia | Sulfated hexose | Sulfatase | hexosaminidase | GlcNAc or GalNAc |
| Hypermucinemia | Sulfated uronic acid | Sulfatase | Iduronidase or glucouronidase | IdoA or GlcA |
| Hyper O-linked glycanemia | Sialic Acid | Sialidase | | Sialic acid |
| Hyper O-linked glycanemia | Sialic Acid | Alpha 2,8 Sialidase | | Sialic acid |
| Hyper O-linked glycanemia | Sialic Acid | Alpha 2,3 Sialidase | | Sialic acid |
| Hyper O-linked glycanemia | Sialic Acid | Alpha 2,6 Sialidase | | Sialic acid |
| Hyper O-linked glycanemia | GalNAc | Hexosaminidase | | GalNAc |
| Hyper O-linked glycanemia | GalNAc | Sialidase | Hexosaminidase | GalNAc |
| Hyper O-linked glycanemia | Sialic acid | Hexosaminidase | Sialidase | Sialic acid |
| Hyper O-linked glycanemia | Galactose | galactosidase | | Galactose |
| Hyper O-linked glycanemia | Galactose | sialidase | galactosidase | Galactose |
| Hyper O-linked glycanemia | Fucose | fucosidase | | Fucose |
| Hyper O-linked glycanemia | Galactose | Galactosidase | | Galactose |
| Hyper O-linked glycanemia | GlcNAc | hexosaminidase | | GlcNAc |
| Hyper O-linked glycanemia | Sulfate | Sulfatase | | Sulfate |
| Hyper O-linked glycanemia | Sulfated hexose | Sulfatase | hexosaminidase | GlcNAc or GalNAc |
| Hyper O-linked glycanemia | Sulfated uronic acid | Sulfatase | Iduronidase or glucouronidase | IdoA or GlcA |
| Hyper N-linked glycanemia | Sialic Acid | Sialidase | | Sialic acid |

TABLE 3-continued

| Disease | Non-Reducing End Structure | Primary Liberating Enzyme | Secondary Liberating Enzyme | Glycan Residual Compound |
|---|---|---|---|---|
| Hyper N-linked glycanemia | Sialic Acid | Alpha 2,8 Sialidase | | Sialic acid |
| Hyper N-linked glycanemia | Sialic Acid | Alpha 2,3 Sialidase | | Sialic acid |
| Hyper N-linked glycanemia | Sialic Acid | Alpha 2,6 Sialidase | | Sialic acid |
| Hyper N-linked glycanemia | GalNAc | Hexosaminidase | | GalNAc |
| Hyper N-linked glycanemia | GalNAc | Sialidase | Hexosaminidase | GalNAc |
| Hyper N-linked glycanemia | Sialic acid | Hexosaminidase | Sialidase | Sialic acid |
| Hyper N-linked glycanemia | Galactose | galactosidase | | Galactose |
| Hyper N-linked glycanemia | Galactose | sialidase | galactosidase | Galactose |
| Hyper N-linked glycanemia | Fucose | fucosidase | | Fucose |
| Hyper N-linked glycanemia | Galactose | Galactosidase | | Galactose |
| Hyper N-linked glycanemia | GlcNAc | hexosaminidase | | GlcNAc |
| Hyper N-linked glycanemia | Sulfate | Sulfatase | | Sulfate |
| Hyper N-linked glycanemia | Sulfated hexose | Sulfatase | hexosaminidase | GlcNAc or GalNAc |
| Hyper N-linked glycanemia | Sulfated uronic acid | Sulfatase | Iduronidase or glucouronidase | IdoA or GlcA |
| Hypersialylemia | Sialic Acid | Sialidase | | Sialic acid |
| Hypersialylemia | Sialic Acid | Alpha 2,8 Sialidase | | Sialic acid |
| Hypersialylemia | Sialic Acid | Alpha 2,3 Sialidase | | Sialic acid |
| Hypersialylemia | Sialic Acid | Alpha 2,6 Sialidase | | Sialic acid |
| Hypersialylemia | GalNAc | Hexosaminidase | | GalNAc |
| Hypersialylemia | GalNAc | Sialidase | Hexosaminidase | GalNAc |
| Hypersialylemia | Sialic acid | Hexosaminidase | Sialidase | Sialic acid |
| Hypersialylemia | Galactose | galactosidase | | Galactose |
| Hypersialylemia | Galactose | sialidase | galactosidase | Galactose |
| Hypersialylemia | Fucose | fucosidase | | Fucose |
| Hypersialylemia | Galactose | Galactosidase | | Galactose |
| Hypersialylemia | GlcNAc | hexosaminidase | | GlcNAc |
| Hypersialylemia | Sulfate | Sulfatase | | Sulfate |
| Hypersialylemia | Sulfated hexose | Sulfatase | hexosaminidase | GlcNAc or GalNAc |
| Hypersialylemia | Sulfated uronic acid | Sulfatase | Iduronidase or glucouronidase | IdoA or GlcA |
| Hyperfucosylemia | Sialic Acid | Sialidase | | Sialic acid |
| Hyperfucosylemia | Sialic Acid | Alpha 2,8 Sialidase | | Sialic acid |
| Hyperfucosylemia | Sialic Acid | Alpha 2,3 Sialidase | | Sialic acid |
| Hyperfucosylemia | Sialic Acid | Alpha 2,6 Sialidase | | Sialic acid |
| Hyperfucosylemia | GalNAc | Hexosaminidase | | GalNAc |
| Hyperfucosylemia | GalNAc | Sialidase | Hexosaminidase | GalNAc |
| Hyperfucosylemia | Sialic acid | Hexosaminidase | Sialidase | Sialic acid |
| Hyperfucosylemia | Galactose | galactosidase | | Galactose |
| Hyperfucosylemia | Galactose | sialidase | galactosidase | Galactose |
| Hyperfucosylemia | Fucose | fucosidase | | Fucose |
| Hyperfucosylemia | Galactose | Galactosidase | | Galactose |
| Hyperfucosylemia | GlcNAc | hexosaminidase | | GlcNAc |
| Hyperfucosylemia | Sulfate | Sulfatase | | Sulfate |
| Hyperfucosylemia | Sulfated hexose | Sulfatase | hexosaminidase | GlcNAc or GalNAc |
| Hyperfucosylemia | Sulfated uronic acid | Sulfatase | Iduronidase or glucouronidase | IdoA or GlcA |
| Hypersulfogycanemia | Sialic Acid | Sialidase | | Sialic acid |
| Hypersulfogycanemia | Sialic Acid | Alpha 2,8 Sialidase | | Sialic acid |
| Hypersulfogycanemia | Sialic Acid | Alpha 2,3 Sialidase | | Sialic acid |
| Hypersulfogycanemia | Sialic Acid | Alpha 2,6 Sialidase | | Sialic acid |

TABLE 3-continued

| Disease | Non-Reducing End Structure | Primary Liberating Enzyme | Secondary Liberating Enzyme | Glycan Residual Compound |
|---|---|---|---|---|
| Hypersulfogycanemia | GalNAc | Hexosaminidase | | GalNAc |
| Hypersulfogycanemia | GalNAc | Sialidase | Hexosaminidase | GalNAc |
| Hypersulfogycanemia | Sialic acid | Hexosaminidase | Sialidase | Sialic acid |
| Hypersulfogycanemia | Galactose | galactosidase | | Galactose |
| Hypersulfogycanemia | Galactose | sialidase | galactosidase | Galactose |
| Hypersulfogycanemia | Fucose | fucosidase | | Fucose |
| Hypersulfogycanemia | Galactose | Galactosidase | | Galactose |
| Hypersulfogycanemia | GlcNAc | hexosaminidase | | GlcNAc |
| Hypersulfogycanemia | Sulfate | Sulfatase | | Sulfate |
| Hypersulfogycanemia | Sulfated hexose | Sulfatase | hexosaminidase | GlcNAc or GalNAc |
| Hypersulfogycanemia | Sulfated uronic acid | Sulfatase | Iduronidase or glucouronidase | IdoA or GlcA |

Provided herein are methods of diagnosing individuals (including, e.g., a disease state or the severity of a disease states) with an infectious disease state associated with abnormal glycan accumulation. Provided in Table 4 are specific embodiments of disease that are optionally diagnosed and/or monitored according to various embodiments described herein. Table 4 also illustrates various non-limiting embodiments of specific enzyme(s) that are optionally utilized to treat a biological sample from an individual suffering from or suspected of (e.g., through a pre- or preliminary screening process) suffering from various infectious disease states associated with abnormal glycan accumulation. Moreover, Table 4 further illustrates various glycan residual compounds that are liberated in various embodiments described herein, such liberated glycan residual compounds optionally being detected and/or measured in order to diagnose and/or monitor various infectious disease states.

TABLE 4

Infectious Diseases

| Disease | Non-Reducing end structure | Primary Liberating Enzyme | Secondary Liberating Enzyme | Glycan Residual Compound |
|---|---|---|---|---|
| Bacterial Infections | Mannose | Mannosidase | | Mannose |
| Bacterial Infections | Fucose | Fucosidase | | Fucose |
| Bacterial Infections | Glucose | Glucosidase | | Glucose |
| Bacterial Infections | Galactose | Galactosidase | | Galactose |
| Bacterial Infections | GlcNAc | hexosaminidase | | GlcNAc |
| Bacterial Infections | GalNAc | hexosaminidase | | GalNAc |
| Bacterial Infections | Arabinose | Arabinosidase | | Arabinose |
| Bacterial Infections | Xylose | Xylosidase | | Xylose |
| Bacterial Infections | Ribose | Ribosidase | | Ribose |
| Bacterial Infections | Lyxose | Lyxosidase | | Lyxose |
| Bacterial Infections | Talose | Talosidase | | Talose |
| Bacterial Infections | Idose | Idosidase | | Idose |
| Bacterial Infections | Gulose | Gulosidase | | Gulose |
| Bacterial Infections | Altrose | Altrosidase | | Altrose |
| Bacterial Infections | Allose | Allosidase | | Allose |
| Fungal Infections | Mannose | Mannosidase | | Mannose |
| Fungal Infections | Fucose | Fucosidase | | Fucose |
| Fungal Infections | Glucose | Glucosidase | | Glucose |
| Fungal Infections | Galactose | Galactosidase | | Galactose |
| Fungal Infections | GlcNAc | hexosaminidase | | GlcNAc |
| Fungal Infections | GalNAc | hexosaminidase | | GalNAc |
| Fungal Infections | Arabinose | Arabinosidase | | Arabinose |
| Fungal Infections | Xylose | Xylosidase | | Xylose |
| Fungal Infections | Ribose | Ribosidase | | Ribose |
| Fungal Infections | Lyxose | Lyxosidase | | Lyxose |
| Fungal Infections | Talose | Talosidase | | Talose |
| Fungal Infections | Idose | Idosidase | | Idose |
| Fungal Infections | Gulose | Gulosidase | | Gulose |
| Fungal Infections | Altrose | Altrosidase | | Altrose |
| Fungal Infections | Allose | Allosidase | | Allose |
| Viral Infections | Sialic Acid | Sialidase | | Sialic acid |
| Viral Infections | Sialic Acid | Alpha 2,8 Sialidase | | Sialic acid |
| Viral Infections | Sialic Acid | Alpha 2,3 Sialidase | | Sialic acid |
| Viral Infections | Sialic Acid | Alpha 2,6 Sialidase | | Sialic acid |
| Viral Infections | GalNAc | Hexosaminidase | | GalNAc |
| Viral Infections | GalNAc | Sialidase | Hexosaminidase | GalNAc |

TABLE 4-continued

Infectious Diseases

| Disease | Non-Reducing end structure | Primary Liberating Enzyme | Secondary Liberating Enzyme | Glycan Residual Compound |
|---|---|---|---|---|
| Viral Infections | Sialic acid | Hexosaminidase | Sialidase | Sialic acid |
| Viral Infections | Galactose | galactosidase | | Galactose |
| Viral Infections | Galactose | sialidase | galactosidase | Galactose |
| Viral Infections | Fucose | fucosidase | | Fucose |
| Viral Infections | Galactose | Galactosidase | | Galactose |
| Viral Infections | GlcNAc | hexosaminidase | | GlcNAc |
| Viral Infections | Sulfate | Sulfatase | | Sulfate |
| Viral Infections | Sulfated hexose | Sulfatase | hexosaminidase | GlcNAc or GalNAc |
| Viral Infections | Sulfated uronic acid | Sulfatase | Iduronidase or glucouronidase | IdoA or GlcA |

Figure 2:
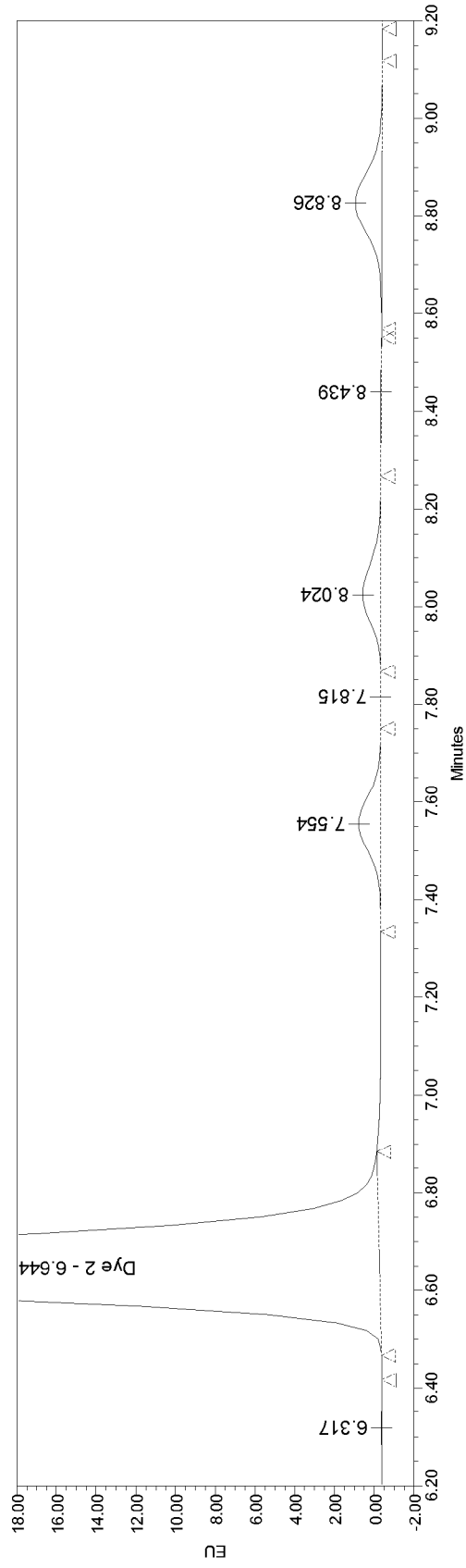
FIG. 2 illustrates compounds present in a normal biological subject to an enzymatic glycan residual liberation process described herein.
Figure 3:
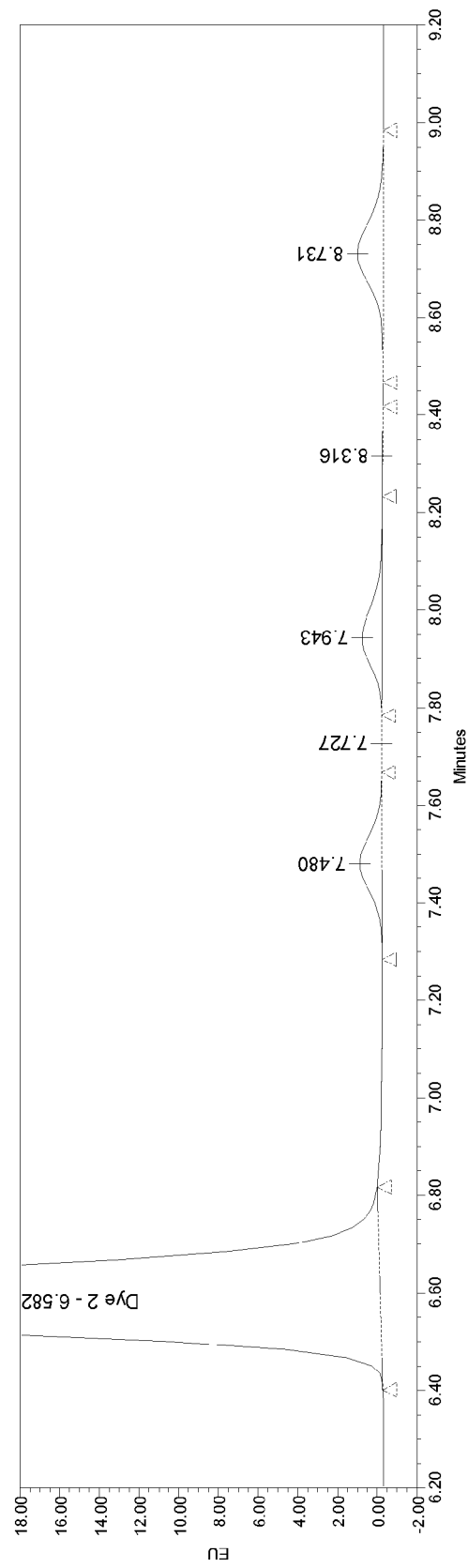
FIG. 3 illustrates compounds present in a biological sample of an individual suffering from a disorder associated with abnormal glycan accumulation not subject to an enzymatic glycan residual liberation process described herein.
Figure 4:
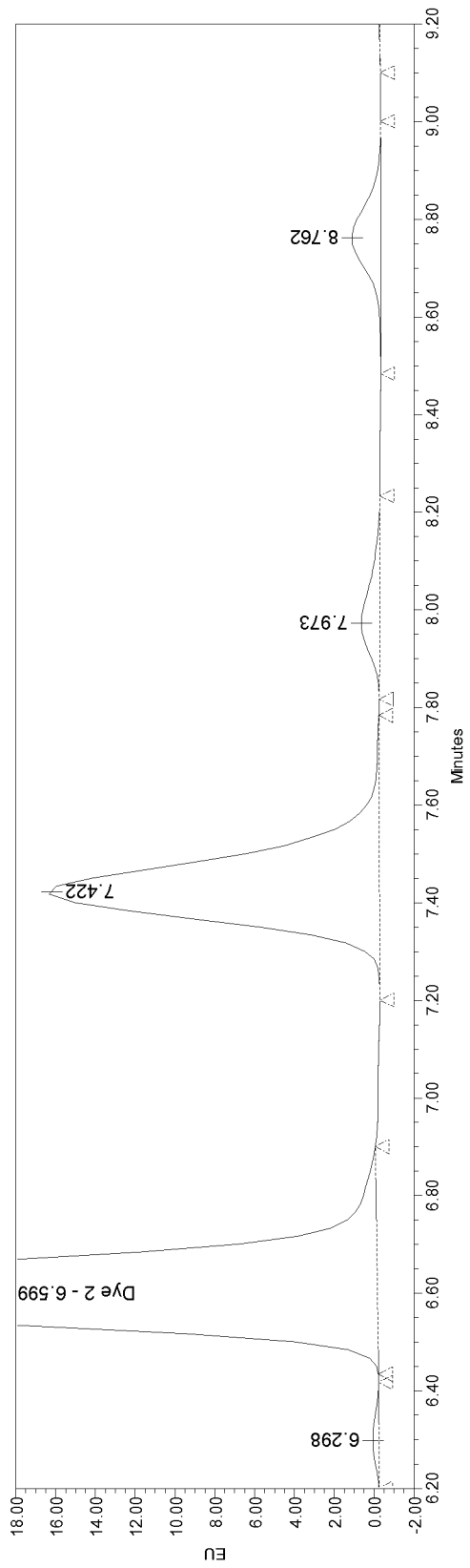
FIG. 4 illustrates compounds present in a biological sample of an individual suffering from a disorder associated with abnormal glycan accumulation subject to an enzymatic glycan residual liberation process described herein.

FIG. 1 illustrates compounds present in a normal biological sample not subject to an enzymatic glycan residual liberation process described herein. FIG. 2 illustrates compounds present in a normal biological subject to an enzymatic glycan residual liberation process described herein. FIG. 3 illustrates compounds present in a biological sample of an individual suffering from a disorder associated with abnormal glycan accumulation not subject to an enzymatic glycan residual liberation process described herein. FIG. 4 illustrates compounds present in a biological sample of an individual suffering from a disorder associated with abnormal glycan accumulation subject to an enzymatic glycan residual liberation process described herein.

Detecting and Measuring:

Glycan residual compounds (including, e.g., oligosaccharides, monosaccharides, sulfate, phosphate, sialic acid, acetate, or the like) described herein are detected and/or measured in processes described herein in any suitable manner. In some embodiments, glycan residual compounds are detected and/or measured in unmodified form. In other embodiments, glycan residual compounds are tagged with a detectable label prior and the labeled glycan residual compound is detected.

In some embodiments, non-labeled compounds are optionally detected and/or measured in any suitable manner, e.g., by pH, by quantitative nuclear magnetic resonance (NMR), or the like.

In various embodiments, a method described herein comprises determining whether the amount of liberated glycan residue is abnormal and such a determination comprises labeling the glycan residue with a detectable label and measuring the amount of labeled glycan residue with an analytical instrument. In specific embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

In the various embodiments of any process or method described herein, any suitable detectable label is optionally utilized. In some embodiments, detectable labels useful in the processes or methods described herein include, by way of non-limiting example, mass labels, antibodies, affinity labels, radioisotope labels, chromophores, fluorescent labels, or the like.

Fluorescent labels suitable for use in various embodiments herein include, by way of non-limiting example, 2-aminopyridine (2-AP), 2-aminobenzoic acid (2-AA), 2-aminobenzamide (2-AB), 2-aminoacridone (AMAC), p-aminobenzoic acid ethyl ester (ABEE), p-aminobenzonitrile (ABN), 2-amino-6-cyanoethylpyridine (ACP), 7-amino-4-methyl-coumarine (AMC), 8-aminonaphthalene-1,3,6-trisulfate (ANTS), 7-aminonaphthalene-1,3-disulfide (ANDS), and 8-aminopyrene-1,3,6-trisulfate (APTS), or the like. The fluorescent labels can be attached by reductive amination with the fluorescent label and sodium cyanoborohydride or the like.

Mass labels suitable for use in various embodiments herein include, by way of non-limiting example, D-2-anthranilic acid, D-2-aminopyridine, D-methyl iodide, $^{13}C$ methyl iodide, deuterated-pyridyl-amine, D-biotin or the like. The mass labels can be attached by permethylation or reductive amination by any method that is known to those of skill in the art.

Affinity labels suitable for use in various embodiments herein include, by way of non-limiting example, biotin and derivatives.

Radioisotope labels suitable for use in various embodiments herein include, by way of non-limiting example, sodium borotritide ($NaB^3H_4$), $^3H$, $^{14}C$, $^{32}P$, $^{35}S$, or the like.

Chromophores suitable for use in various embodiments herein include, by way of non-limiting example, 4-amino-1, 1'-azobenzene, 4'-N,N-dimethylamino-4-aminoazobenzene, aminoazobenzene, diaminoazobenzene, Direct Red 16, CI Acid Red 57, CI Acid Blue 45, CI Acid Blue 22, CL Mordant Brown 13, CI Direct Orange 75, or the like. The chromophores may be labeled by any method that is known to those of skill in the art, such as reductive amination with the chromophore and sodium cyanoborohydride.

In some embodiments, the detectable label is an antibody. In specific embodiments, the antibody is attached to a detectable compound, such as mass labels, radioisotope labels, chromophores, fluorescent labels, or the like. In some embodiments, antibodies are themselves detected and/or are detectable in various manners, e.g., as a chromophore, a fluorophore, or the like; or with a probe (e.g., using dot blot techniques, immune-detection techniques, or the like).

In certain embodiments, detectable labels are detected and/or quantified according to any process described herein using any technique, particularly any technique suitable for the detectable label utilized. In some embodiments, suitable detection techniques include, by way of non-limiting example, one or more of a mass spectrometer, a nuclear magnetic resonance spectrometer, a UV-Vis spectrometer, an IR spectrometer, a fluorimeter, a phosphorimeter, a radiation spectrometer (e.g., a scintillation counter), a thin layer chromatographic technique, or the like. In certain embodiments, in any process described herein, glycan residual compounds are optionally directly detected using a suitable technique, such as quantitative nuclear magnetic resonance. Quantitative nuclear magnetic resonance is also optionally utilized to quantify and/or detect the presence of a detectable label. In certain embodiments, one or more glycan residual compounds are optionally detected using a suitable liquid chromatography mass spectrometer (LC-MS).

In some embodiments, glycan residual compounds are tagged with an antibody or probe, and are quantified using any suitable method (e.g., dot blot techniques, immune detection techniques (e.g., ELISA), or the like).

Various analytical methods useful for the processes described herein include, by way of non-limiting example, mass spectrometry, chromatography, HPLC, UPLC, TLC, GC, HPAEC-PAD, electrophoresis—capillary or gel, or the like. In certain embodiments, wherein a chromatographic technique is utilized, any suitable solvent system is optionally employed. In certain embodiments, a column (e.g., Cosmogel DEAE, Tsk Gel DEAE, Cosmogel QA, Cosmogel CM, Cosmogel SP, or the like) is optionally loaded with an equilibrating solvent (e.g., a buffer or salt solution, such as a potassium acetate solution, sodium chloride solution, sodium acetate solution, ammonium acetate solution, or the like), e.g., with a pH of about 6, 7, or 8. In some embodiments, the buffer or salt solution has a concentration of about 10 mM, 20 mM, 30 mM, 50 mM, 100 mM, 500 mM, 1 M, 2 M, or the like. Any suitable flow rate is used, e.g., 0.5 mL/min, 1 mL, min, 1.5 mL/min, 2 mL/min, or the like. Following equilibration, a linear gradient is optionally utilized. In some embodiments, the linear gradient is run over 1-20 min, 1-10 min, 10-20 min, 1-5 min, 5-10 min, or the like. In certain embodiments, the gradient is a buffer or salt solution, e.g., as described above (e.g., from 0 M to 0.5 M, from 0 M to 3 M, from 0.5 M to 2 M, from 0 M to 2 M, from 1 M to 2 M, from 0 M to 3 M, from 2 M to 0 M, from 3 M to 0 M, or the like). Once the gradient has reached a final concentration, the eluent is optionally held at the final concentration for a suitable period of time (e.g., 1-20 min, 5-10 min, 10-15 min, 1-5 min, 1-10 min, 15-20 min, or the like). After the optional holding of the final concentration, the eluent may be switched to a second solvent or solvent system (e.g., an alcohol, such as methanol, ethanol, or isopropanol, acetonitrile, water, or the like). The switch to the second solvent system may be over a period of time, e.g., 15 seconds, 30 seconds, 45 seconds, 60 seconds, 2 min, 3 min, or the like. The second solvent system is optionally held for a period of time, such as 1 min, 2 min, 3 min, 4 min, 5 min, 6 min, or the like. Following the second solvent system cycle, the column is optionally restored to initial solvent conditions.

Purification:

In certain embodiments, methods described herein comprise purifying a biological sample, e.g., to remove non-glycan compounds from the biological sample. In some embodiments, a biological sample is purified prior to transforming a glycan thereof.

In certain embodiments, a biological sample containing glycans (purified or not) can also be prepared so that all free glycan residual compounds (e.g., monosaccharides) that are naturally present in the biological sample (i.e., as taken from an individual and without being treated) are eliminated from the sample to reduce background signal (for example using dialysis, spin column, gel filtration, etc).

In some embodiments, any process described herein includes a step of purifying a biological sample comprising removing monosaccharides therefrom, removing sulfates therefrom, removing phosphates therefrom, removing acetate therefrom, removing sialic acid therefrom, or a combination thereof. For example, in some embodiments, a biological sample is optionally placed in to a defined MW cut off spin column (retains large molecules when spun), optionally washed (e.g., with 1 or more volumes of water or buffer), and/or the like.

In certain embodiments, purification of biological samples may further or alternatively comprise, e.g., fractionation, purification, enrichment, or the like of glycans contained therein. In some instances, such purification techniques are suitable to isolate and/or separate different glycan classes within the biological sample prior to transformation of one or more of such glycans. In more specific instances, such purification techniques are used to isolate and/or separate different subsets of a single glycan class (such as isolating complex N-linked glycans from hybrid N-linked structures) prior to transformation of one or more of such glycans. In certain embodiments, a biological sample is optionally prepared in such a way to enrich for specific glycan classes. For example, a PHA affinity column is optionally used to isolate a sub-fraction of complex N-linked glycans while a Con A column could be used to enrich in a different subset of N-linked glycans.

In some embodiments, any process described herein comprises purification of a glycan residual compound resulting from a process described herein (e.g., purification of the glycan residual compound prior to analysis thereof). For example, in some embodiments, the glycan residual compound is optionally isolated by any suitable process, such as by washing the free glycan residual compound (e.g., through a defined MW cut off membrane or by any other suitable method). Moreover, in certain embodiments, the resulting isolated glycan residual compound containing composition is optionally dried or otherwise treated to concentrate the sample and subsequently analyzed for glycan residual compound content by any suitable analytical technique.

In some embodiments, the processes described herein comprises further treatment steps of the test and/or control samples. For example, in some embodiments, the samples are homogenized and/or purified. In specific embodiments homogenization is achieved in any suitable manner including, by way of non-limiting example, with a basic solution, sonication, tissue grinding, or other chemical agents. In some embodiments, severity of a disorder is determined if a certain threshold amount is measured (e.g., as compared to a control or controls) or a threshold signal (e.g., on a fluorimeter or other analytical device utilized to detect and/or measure the generated biomarker). Similarly, a carrier of a disorder described herein is, in certain embodiments, determined if a certain threshold amount is measured (e.g., as compared to a control or controls) or a threshold signal (e.g., on a fluorimeter or other analytical device utilized to detect and/or measure the generated biomarker).

In certain embodiments, samples, including test samples and/or control samples, described herein are optionally purified prior to glycan processing (e.g., lyase treatment) and/or characterization. Test samples and/or control samples (i.e., one or more or all of the glycans found therein) are optionally purified using any suitable purification technique. Test samples and/or control samples are optionally purified at any suitable point in a process described herein, including before or after tagging of the glycans founds within the sample. In certain embodiments, purification techniques include centrifugation, electrophoresis, chromatography (e.g., silica gel or alumina column chromatography), gas chromatography, high performance liquid chromatography (HPLC) (e.g., reverse phase HPLC on chiral or achiral columns), thin layer chromatography, ion exchange chromatography, gel chromatography (e.g., gel filtration or permeation or size exclusion chromatography, gel electrophoresis), molecular sieve chromatography, affinity chromatography, size exclusion, filtration (e.g. through a florisil or activated charcoal plug), precipitation, osmosis, recrystallization, fluorous phase purification, distillation, extraction, chromatofocusing, supercritical fluid extraction, preparative flash chromatography (e.g., flash chromatography using a UV-Vis detector and/or a mass spectrometer (e.g., using the Biotage® suite of products) or the like.

In some embodiments, glycans, such as heparan sulfate, are naturally found attached to a core protein (together forming a proteoglycan) or a lipid. In some embodiments, provided herein are purification processes of separating glycan fragments (e.g., heparan sulfate fragments) from proteoglycans or glycolipids prior to processing the glycan for processing and analysis.

Monitoring Therapy

Provided in certain embodiments are methods of treating disorders associated with the abnormal degradation, biosynthesis and/or accumulation of glycans, the methods comprising:
a. administering an agent for treating disorders associated with the abnormal degradation, biosynthesis and/or accumulation of glycans (e.g., an anti-LSD agent, an anti-cancer agent, or the like) to an individual in need thereof;
b. monitoring the accumulation of glycans in the individual using any process described herein for detecting or quantifying the amount of glycan residual compounds (e.g., mono-saccharides, sulfate, or the like) present in a lyase digested biological sample (e.g., urine, serum, plasma, or CSF sample) according to any process described herein.

Provided in further or alternative embodiments are methods of monitoring the treatment of disorders associated with the abnormal degradation, biosynthesis and/or accumulation of glycans, the methods comprising the following steps:
a. following administration of an agent for treating a disorder associated with the abnormal degradation, biosynthesis and/or accumulation of glycans (e.g., an anti-LSD agent, an anti-cancer agent, or the like) to an individual in need thereof, generating a biomarker comprising of one or more non-reducing end glycan residual compound (e.g., monosaccharide).

In some embodiments, the biomarker is a saturated monosaccharide and is generated by treating a population of glycans, in or isolated from a biological sample from the individual, with at least one digesting glycan enzymes, wherein prior to enzyme treatment, the biomarker is not present in abundance in samples from individuals with the disease or condition relative to individuals without the disease or condition. In certain embodiments, monitoring of the accumulation of glycans comprises using an analytical instrument to detect the presence of and/or measure the amount of the biomarker produced and displaying or recording the presence of or a measure of a population of the biomarker; wherein the presence of and/or measure the amount of the biomarker is utilized to monitor the treatment.

In some embodiments, the agent is administered one or more times. In certain embodiments, the agent is administered multiple times. In some embodiments, the agent is administered in a loading dose one or more times (e.g., in a loading dosing schedule) and subsequently administered in a maintenance dose (e.g., in a maintenance dosing schedule, such as three times a day, twice a day, once a day, once every two days, once every three days, once every four days, once a week, or the like). In some embodiments, when glycan (as measure by one or more glycan residual compound(s)) accumulation begins to increase or accelerate, the dose is optionally adjusted (e.g., the maintenance dose is increased, or an additional loading dose or dosing schedule is utilized).

In some embodiments, monitoring the accumulation of glycans comprises repeating the step of: using an analytical instrument to detect the presence of and/or measure the amount of a population of one or more glycan residual compounds present in a transformed biological sample that has been prepared by treating a population of glycans, in or isolated from a biological sample from the individual, with at least one digesting glycan lyase to transform the glycan into the population of the one or more glycan residual compounds. In specific embodiments, the step is repeated at periodic intervals (e.g., every day, every other day, every 2 days, every 3 days, every 4 days, every week, every month, every 3 months, quarterly, every 6 months, yearly, or the like), at regular times following a dose (e.g., 4 hours after a administration of the agent, 6 hours after administration of the agent, 8 hours after administration of the agent, 12 hours after administration of the agent, or the like), prior to administration of the dose (e.g., immediately prior to administration of the agent, 2 hours prior to administration of the agent, or the like), or any other monitoring schedule.

In some embodiments, the monitoring of the accumulation of glycan is conducted over a period of time, e.g., over a week, two weeks, a month, two months, three months, six months, a year, or the like. In some embodiments, the method for quantifying the amount of one or more glycan residual compounds in a lyase digested biological sample (e.g., urine, serum, plasma, or CSF) comprises detecting and/or measuring (e.g., with an analytical device), one or more glycan residual compounds within the lyase digested biological sample from the individual after the biological sample obtained from the individual has been treated with one or more glycan lyases. In certain embodiments, such glycan lyases are suitable for preparing glycan residual compounds from the glycan present in the biological sample obtained from the individual. In certain instances a representative portion of the one or more glycan residual compounds in the transformed biological sample is tagged with any suitable detectable label (e.g., a mass label, a radioisotope label, a fluorescent label, a chromophore label, affinity label, an antibody). In some embodiments, the process comprises displaying or recording such a characterization of the population of glycan residual compounds and/or tagged glycan residual compounds.

In some embodiments, the agent described in a therapy herein includes glycan accumulation inhibitors, agents that promote glycan degradation, agents that activate enzymes that degrade glycans, agents that inhibit biosynthesis of glycans, or the like. In some embodiments, the agent that modulates glycan biosynthesis is an agent that selectively modulates heparan sulfate biosynthesis, an agent that selectively modulates chondroitin sulfate biosynthesis, an agent that selectively modulates dermatan sulfate biosynthesis, an agent that selectively modulates keratan sulfate biosynthesis, an agent that selectively modulates hyaluronan biosynthesis, or a combination thereof. Anti-LSD drugs include, by way of non-limiting example, Imiglucerase (Cerazyme), laronidase (Aldurazyme), idursulfase (Elaprase), galsulfase (Naglazyme), agalsidase beta (Fabrazyme), alglucosidase alfa (Myozyme), agalsidase alfa (Replagal), miglustat (Zavesca).

In some embodiments, one or more of the anti-cancer agents are proapoptotic agents. Examples of anti-cancer agents include, by way of non-limiting example: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents include inhibitors of mitogen-activated protein kinase signaling, e.g., U0126, PD98059, PD184352, PD0325901, ARR$^y$-142886, SB239063, SP600125, BAY 43-9006, wortmannin, or LY294002; Syk inhibitors; mTOR inhibitors; and antibodies (e.g., rituxan).

Other anti-cancer agents include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; anatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine;

losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In some instances, the detection and/or the quantification of the identity and/or amount of glycan residual compounds present in a biological sample is used to identify and/or diagnose a disorder associated with abnormal degradation, biosynthesis and/or accumulation of glycan in an individual suspected of having such a disorder.

In some instances, the detection and/or the quantification of the identity and/or amount of glycan residual compounds present in the biological sample is used to monitor severity and course of the disease in an individual diagnosed with or suspected of having a disorder associated with the abnormal degradation, biosynthesis and/or accumulation of glycans. In some instances, the detection and/or the quantification of the identity and/or amount of glycan residual compounds present in the biological sample is used to calculate the administered dose of an agent that modulates (e.g., promotes and/or inhibits) glycan biosynthesis and/or degradation.

In certain instances, wherein following administration of a selected dose of a therapeutic agent utilized in a therapeutic method described herein, an individual's condition does not improve, the detection and/or the quantification of the identity and/or amount of glycan residual compounds present in a biological sample provides for a treatment regimen to be modified depending on the severity and course of the disease, disorder or condition, previous therapy, the individual's health status and response to the drugs, and the judgment of the treating physician.

In certain embodiments, monitoring the accumulation of glycans in the individual comprises detecting or quantifying the amount of an glycan residual compounds (or one or more glycan residual compounds) in a sample obtained from the individual (e.g., according to any method described herein) to obtain a first accumulation result (e.g., an initial reading before treatment has begun, or at any other time) and a second accumulation result that is subsequent to obtaining the first result. In some embodiments, the second result is compared to the first result to determine if the treatment is effectively reducing, maintaining, or reducing the rate of increasing the glycan residual compounds levels in a substantially identically obtained sample from the individual being treated. In certain embodiments, depending on the difference between the first and second results, the treatment can be altered, e.g., to increase or decrease the amount of agent administered; to substitute the therapeutic agent with an alternative therapeutic agent; or the like. In certain embodiments, the dose of the therapeutic agent is decreased to a maintenance level (e.g., if the glycan residual compound level has been reduced sufficiently); further monitoring of glycan residual compound levels is optional in such situation, e.g., to ensure that reduced or maintained levels of glycan residual compounds (e.g., monosaccharide(s)) are achieved.

Alternatively, provided herein is a method of detecting response to therapy in an individual or a method of predicting response to therapy in an individual comprising:
  a. administering an agent for treating a disorder associated with the abnormal degradation, biosynthesis and/or accumulation of glycans to a plurality of cells from an individual in need thereof (e.g., a plurality of fibroblasts, serum, plasma, or CSF cells from a human suffering from a disorder associated with the abnormal degradation, biosynthesis and/or accumulation of glycans, such as an LSD or cancer);
  b. monitoring the accumulation of glycans in the plurality of cells using any process described herein for detecting or quantifying the amount of glycan residual compounds (e.g., monosaccharides, sulfate, sialic acid, phosphate, acetate, or the like) present in a lyase digested biological sample from the plurality of cells according to any process described herein.

In specific embodiments, the glycan residual compound(s) detected or measured is one or more monosaccharide. It is to be understood that a plurality of cells from an individual includes cells that are directly taken from the individual, and/or cells that are taken from an individual followed by culturing to expand the population thereof.

EXAMPLES

Example 1

To illustrate the methods described herein, we have used human urine sample from normal patients and patients diagnosed with MPS IIIA. MPS IIIA patients have reduced function of the lysosomal enzyme that de-N-sulfates the nonreducing end glucosamine residues present in heparan sulfate. This unique nonreducing end glycan residual (N-sulfated GlcN) can be liberated by treating the glycans with heparin lyases and quantified by fluorescent detection on HPLC. As shown below, glycans prepared in this manner from normal individuals lack N-sulfate GlcN while MPS IIIA patients have a very high level.

Purification: The biological sample (cells, tissue, blood, serum, or the like) is homogenized and solublized in 0.1-1.0 N NaOH (e.g., 0.1N, 0.2 N, 0.3 N, 0.4 N, 0.5 N, 0.6 N, 0.7 N, 0.8 N, 0.9 N, or 1.0 N) or acetic acid and then neutralized with acetic acid or NaOH. Next a small sample is taken to measure protein content of the sample using standard methods. 0.01-0.5 mg/mL (0.01 mg/mL, 0.07 mg/mL, 0.12 mg/mL, 0.17 mg/mL, 0.22 mg/mL, 0.27 mg/mL, 0.32 mg/mL, 0.37 mg/mL, 0.42 mg/mL, or 0.5 mg/mL) protease (trypsin, chymotrypsin, pepsin, pronase, papain, or elastase) is treated in 0.1-0.5 M (e.g., 0.1 n 0.16 M, 0.23 M, 0.32 M, 0.39 M, 0.44 M, or 0.5 M) NaCl, 0.01-0.1 M (e.g., 0.01 M, 0.02 M, 0.04 M, 0.06 M, 0.08 M, 0.1 M) NaOAc, at pH 5.5-7.5 (e.g., 5.5, 6.0, 6.5, 7.0, or 7.5) and 25-40 C (e.g., 25 C, 30 C, 35 C, or 40 C) for 1-24 hours (e.g., 1 h, 2 h, 4 h, 6 h, 8 h, 12 h, 18 h, 24 h). The sample is diluted to reduce the ionic strength and loaded onto an ion exchange column in 5-100 mM (e.g., 5 mM, 10 mM, 20 mM, 30 mM, 40 mM, 50 mM, 60 mM, 70 mM, 75 mM, 80 mM, 90 mM, 95 mM, 100 mM) NaOAc pH 5-7 with 0-300 mM NaCl. After washing, the bound glycosaminoglycans are eluted with 5-100 mM NaOAc pH 5-7 (e.g., 5, 5.5, 6, 6.5, 7) with 0.8-3 M (e.g., 0.8 M, 1 M, 1.2 M, 1.4 M, 1.6 M, 1.8 M, 2 M, 2.5 M, or 3 M) NaCl. The eluted glycans are then concentrated and desalted by ethanol precipitation, size exclusion, or other methods. The purified glycans are dried for further analysis.

Liberation of non-reducing end residual: The purified glycans are resuspended in 10-300 mM sodium acetate, tris, phosphate, or other suitable buffer, 0.02-1 mM (e.g., 0.02, 0.04, 0.06, 0.08, 0.1, 0.2, 0.3, 0.4, 0.5, 0.6, 0.7, 0.8, 0.9, or 1) calcium acetate, pH 5-8 (e.g., 5, 5.5, 6, 6.5, 7, 7.5, or 8), were digested with heparin lyases I, II, III, I and II, I and III, II and III, or I, II, and III (0.0.15-1.5 milliunits of each in 100-ul reactions, IBEX, Montreal, Canada) at 25 to 37° C. for 1 to 24 hours.

Fluorescent tagging of glycan residual: Dried glycan sample is re-suspended in 2-100 µL 0.003-0.1 M (e.g., 0.003 M, 0.003 M, 0.03 n 0.06 M, 0.1 M) AB, AA, AMAC, or Bodipy dye and incubated at room temperature for 1-120 minutes (e.g., 1-10 min, 10-15 min, 15-20 min, 20-25 min, 25-30 min, 30-40 min, 40-50 min, 50-60 min, 60-90 min, 90-120 min) Next, the reaction is initiated with 2-100 µL (2 µL, 5 µL, 10 µL, 15 µL, 20 µL, 25 µL, 30 µL, 40 µL, 50 µL, 60 µL, 70 µL, 80 µL, 90 µL, or 100 µL) 1 M NaCNBH$_4$ and the reaction is allowed to proceed at 25-100 C. (e.g., 25 C, 30 C, 35 C, 40 C, 50 C, 60 C, 70 C, 80 C, 90 C, 100 C).

Detection of glycan residual: HPLC separation of tagged saccharides was performed utilizing the following conditions: Column types: 130A BEH particle Phenyl (1.7, 2.5, 3.5, 5, or 10 uM particle size), 130A BEH particle C18 (1.7, 2.5, 3.5, 5, or 10 uM particle size), HSS particle C18 (1.8, 3.5, or 5 uM particle size), or 300A BEH particle C18 (1.7, 3.5, 5, 10 uM particle size) with suitable length and internal diameter.

Buffer Conditions:
  A=Ammonium Acetate, Sodium Acetate, or Sodium Chloride (e.g., 0 M, 10 mM, 20 mM, 30 mM, 40 mM, 100 mM, 500 mM, 1 M, 2 M) with 0-20% methanol
  B=100% Alcohol, such as methanol, ethanol, or isopropanol
  Initial Conditions: 70-95% A, 0-30% B
  Flow Rate is constant at 0.05-1 ml/min
  Runs a gradient down to 70-90% A, 10-30% B over 5-65 min
  At 8.1 min runs a gradient to 0-20% A, 80-100% B over 5-20 min 5-65 min returns to initial conditions FIG. 1 illustrates an HPLC trace of eluted compounds detected in normal patient urine not subject to enzymatic glycan residual liberation (i.e., providing background signals). FIG. 2 illustrates an HPLC trace of eluted compounds detected in normal patient urine subject to enzymatic glycan residual liberation as set forth in Example 1. FIG. 3 illustrates an HPLC trace of eluted compounds detected in MPS IIIA patient urine not subject to enzymatic glycan residual liberation (i.e., providing background signals). FIG. 4 illustrates an HPLC trace of eluted compounds detected in MPS IIIA patient urine subject to enzymatic glycan residual liberation.

Example 2

The processes described in Example 1 are repeated and/or modified for the diseases listed in Tables 1-4 utilizing the enzymes described there in and detecting the glycan residual compounds also described therein.

What is claimed is:
1. A method of determining the presence of and/or measuring the amount of a biomarker to determine the presence, identity, and/or severity of the disease or condition in an individual having a disease or condition associated with abnormal glycan biosynthesis, degradation, or accumulation, the method comprising:
  (a) generating the biomarker comprising of one or more non-reducing end glycan residual compound(s), wherein the biomarker is generated by treating a population of glycans, in or isolated from a biological sample from the individual, with at least one digesting glycan enzyme(s), wherein prior to enzyme treatment, the biomarker is not present in abundance in samples from individuals with the disease or condition relative to individuals without the disease or condition, and
  (b) using an analytical instrument to detect the presence of and/or measure the amount of the biomarker produced and displaying or recording the presence of or a measure of a population of the biomarker; and
  (c) determining the presence, identity, and/or severity of the disease or condition utilizing the presence of and/or measure the amount of the biomarker;
  wherein the disease or condition is a lysosomal storage disorder or a neurological disorder; and
  wherein when the lysosomal storage disorder is an MPS disorder, then the digesting glycan enzyme is not a lyase.
2. The method of claim 1, wherein the disease or disorder is caused by an abnormally functioning glycan degradation enzyme and wherein the abnormally functioning glycan degradation enzyme and the normally functioning glycan degradation enzyme are of the same type.
3. The method of claim 1, wherein the abnormal glycan accumulation comprises the accumulation of abnormal amounts of normal glycans.
4. The method of claim 1, wherein the abnormal glycan accumulation comprises the accumulation of abnormal amounts of abnormal glycans.
5. The method of claim 1, wherein the normally functioning glycan degradation enzyme is a glycosidase, sulfatase, phosphorylase, deacetylase, or a combination thereof.
6. The method of claim 5, wherein the normally functioning glycan degradation enzyme is a glycosidase selected from an exo-glycosidase and an endo-glycosidase.
7. The method of claim 6 wherein the glycosidase is an exo-glycosidase selected from the group consisting of a galactosidase, and a glucuronidase.
8. The method of claim 6, wherein the glycan residual compound is a monosaccharide.
9. The method of claim 5, wherein the glycan residual compound is sulfate, phosphate, acetate, or a combination thereof.
10. The method of claim 1, further comprising purifying a biological sample prior to transforming a glycan thereof wherein the process of purifying a biological sample comprises removing monosaccharides therefrom, removing sulfates therefrom, removing phosphates therefrom, removing acetate therefrom, or a combination thereof.
11. The method of claim 1, wherein transforming a glycan of a biological sample with a normally functioning glycan degradation enzyme comprises transforming a glycan of a biological sample with a plurality of normally functioning glycan degradation enzymes concurrently, sequentially, or a combination thereof.
12. The method of claim 1, wherein the disorder associated with an abnormal glycan accumulation is Alzheimer's disease, Parkinson's disease, MPS I, MPS II, MPS IIIA, MPS IVA, MPS VI, Gaucher disease, Krabbe disease, Pompe disease, Sandhoff disease, Tay-Sachs disease, or Fabry Disease.
13. The method of claim 1, wherein determining whether the amount of liberated glycan residue is abnormal comprises labeling the glycan residue with a detectable label and measuring the amount of labeled glycan residue with an analytical instrument using UV-Vis spectroscopy, IR spectroscopy, mass spectrometry, or a combination thereof.
14. The method of claim 13, wherein the detectable label is a mass label, a radioisotope label, a fluorescent label, a chromophore label, or affinity label.
15. The method of claim 1, wherein prior to measuring the amount of a population of non-reducing end glycan residual compounds, the non-reducing end glycan residual compounds are labeled with a detectable label and wherein the amount of liberated glycan is measured using UV-Vis spectroscopy, IR spectroscopy, mass spectrometry, or a combination thereof.
16. The method of claim 15, wherein the detectable label is a mass label, a radioisotope label, a fluorescent label, a chromophore label, or affinity label.
17. A method monitoring the treatment of a disorder associated with the abnormal degradation, biosynthesis and/or accumulation of glycans, the method comprising:
  (a) following administration of an agent for treating a disorder associated with the abnormal degradation, biosynthesis and/or accumulation of glycans to an individual in need thereof, using an analytical instrument to measure the amount of a population of a biomarker comprising non-reducing end glycan residual compounds present in a transformed biological sample, the biomarker being generated by treating a population of glycans, in or isolated from a biological sample from the individual, with at least one digesting glycan enzyme(s), wherein prior to enzyme treatment, the biomarker is not present in abundance in samples from individuals with the disease or condition relative to individuals without the disease or condition, and
  (b) determining whether or not the amount of biomarker has decreased or increased at a slower rate compared to the amount or rate of increase prior to administration of the agent for treating a disorder associated with the abnormal degradation, biosynthesis and/or accumulation of glycans; and
  wherein the disorder is a lysosomal disorder or a neurological disorder.
18. The method of claim 17, wherein the normally functioning glycan degradation enzyme is a glycosidase, sulfatase, phosphorylase, deacetylase, or a combination thereof.

19. The method of claim 18, wherein the normally functioning glycan degradation enzyme is a glycosidase selected from an exo-glycosidase and an endo-glycosidase.

20. The method of claim 17, wherein the glycan residual compound is a monosaccharide, sulfate, phosphate, acetate, or a combination thereof.

21. The method of claim 17, wherein transforming a glycan of a biological sample with a normally functioning glycan degradation enzyme comprises transforming a glycan of a biological sample with a plurality of normally functioning glycan degradation enzymes concurrently, sequentially, or a combination thereof.

* * * * *